United States Patent
Wixey

(10) Patent No.: US 10,772,630 B2
(45) Date of Patent: Sep. 15, 2020

(54) STAPLE PUSHER WITH LOST MOTION BETWEEN RAMPS

(71) Applicant: Intuitive Surgical Operations, Inc., Sunnyvale, CA (US)

(72) Inventor: Matthew A. Wixey, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 197 days.

(21) Appl. No.: 15/772,528

(22) PCT Filed: Oct. 28, 2016

(86) PCT No.: PCT/US2016/059552
§ 371 (c)(1),
(2) Date: Apr. 30, 2018

(87) PCT Pub. No.: WO2017/083126
PCT Pub. Date: May 18, 2017

(65) Prior Publication Data
US 2019/0076142 A1 Mar. 14, 2019

Related U.S. Application Data

(60) Provisional application No. 62/255,129, filed on Nov. 13, 2015.

(51) Int. Cl.
*A61B 17/068* (2006.01)
*A61B 17/072* (2006.01)
(Continued)

(52) U.S. Cl.
CPC ...... *A61B 17/07207* (2013.01); *A61B 17/068* (2013.01); *A61B 34/37* (2016.02);
(Continued)

(58) Field of Classification Search
CPC . A61B 17/068; A61B 17/0686; A61B 17/072; A61B 17/07207
(Continued)

(56) References Cited

U.S. PATENT DOCUMENTS 5,749,893 A * 5/1998 Vidal ............... A61B 17/07207
227/176.1
5,820,009 A * 10/1998 Melling ........... A61B 17/07207
227/176.1
(Continued)

FOREIGN PATENT DOCUMENTS

EP 0267921 B1 4/1994

OTHER PUBLICATIONS

International Search Report and Written Opinion for Application No. PCT/US2016/059552, dated Feb. 7, 2017, 9 pages.
(Continued)

*Primary Examiner* — Praachi M Pathak
(74) *Attorney, Agent, or Firm* — Schwegman Lundberg & Woessner, P.A.

(57) ABSTRACT

A drive shuttle is provided that includes a leader ramp mount that includes a longitudinal first axis; a first leader ramp that depends from (i.e. that physically couples to) a first side of the leader ramp mount; a pusher protrusion that depends from a second side of the leader ramp mount; a follower ramp mount; a follower protrusion that depends from the follower ramp mount; a first follower ramp that depends from the follower protrusion; wherein the first leader ramp, the pusher protrusion, the first follower ramp and the follower protrusion are disposed in relation to each another such that, in the first configuration, the pusher protrusion is spaced apart longitudinally from the follower protrusion by an offset amount and the first leader ramp is aligned longitudinally with the first follower ramp; and in the second
(Continued)

configuration, the pusher protrusion contacts the follower protrusion and the first leader ramp is spaced apart longitudinally from the first follower ramp by the offset amount.

24 Claims, 20 Drawing Sheets

(51) Int. Cl.
*A61B 34/37* (2016.01)
*A61B 34/30* (2016.01)

(52) U.S. Cl.
CPC ........... *A61B 2017/07228* (2013.01); *A61B 2017/07278* (2013.01); *A61B 2034/302* (2016.02)

(58) Field of Classification Search
USPC ........... 606/139; 74/25, 567; 227/19, 175.1, 227/176.1, 178.1, 180.1, 175.2
See application file for complete search history.

(56) References Cited

U.S. PATENT DOCUMENTS

| | | | |
|---|---|---|---|
| 8,573,461 | B2 | 11/2013 | Shelton, IV et al. |
| 8,893,949 | B2* | 11/2014 | Shelton, IV ....... A61B 17/1155 227/176.1 |
| 8,991,678 | B2* | 3/2015 | Wellman ............. A61B 17/072 227/180.1 |
| 2008/0283571 | A1 | 11/2008 | Boyden et al. |
| 2014/0291383 | A1 | 10/2014 | Spivey et al. |
| 2015/0230794 | A1 | 8/2015 | Wellman et al. |
| 2016/0242773 | A1* | 8/2016 | Sadowski ............ A61B 17/072 |
| 2019/0076142 | A1* | 3/2019 | Wixey ................ A61B 17/068 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

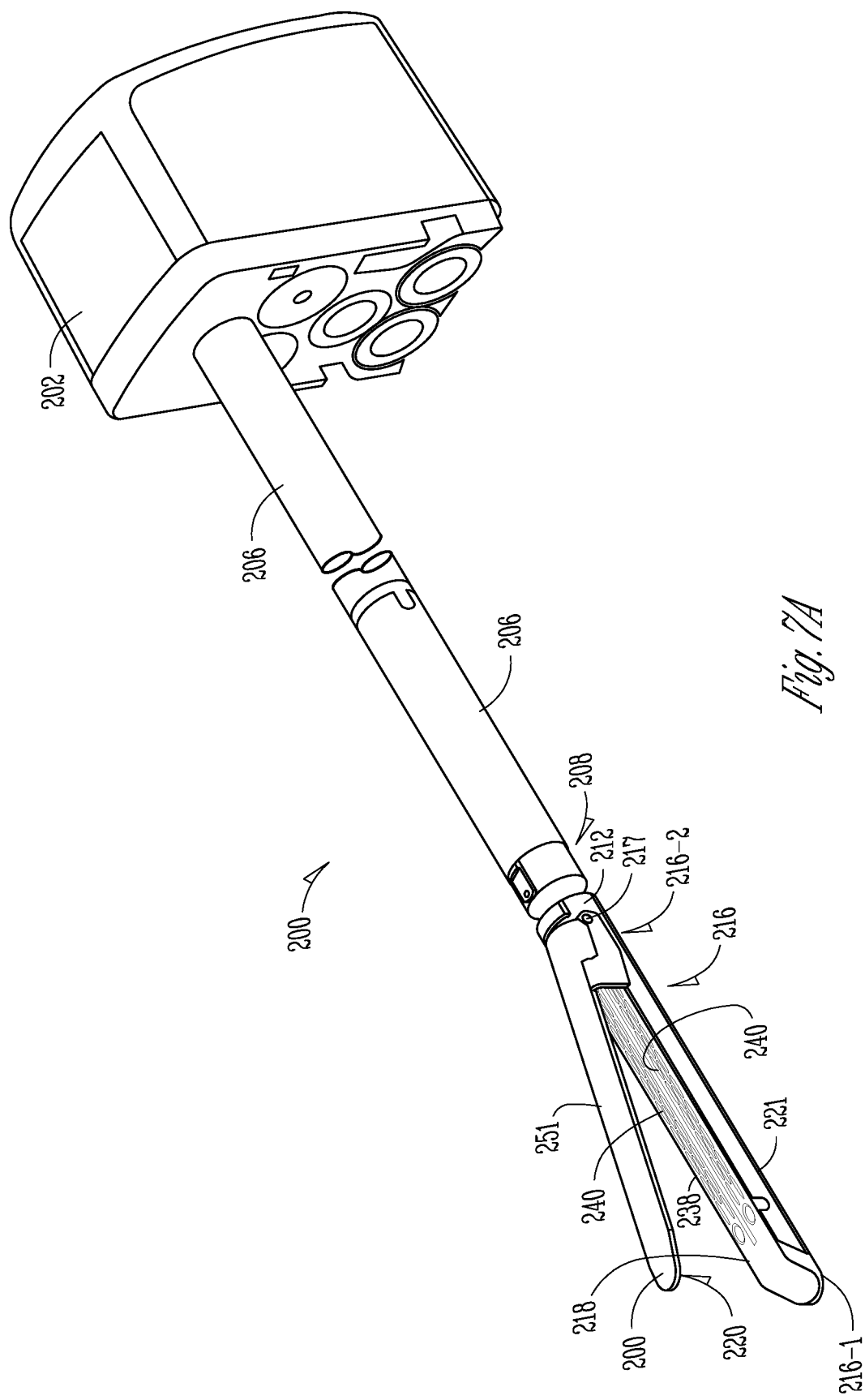

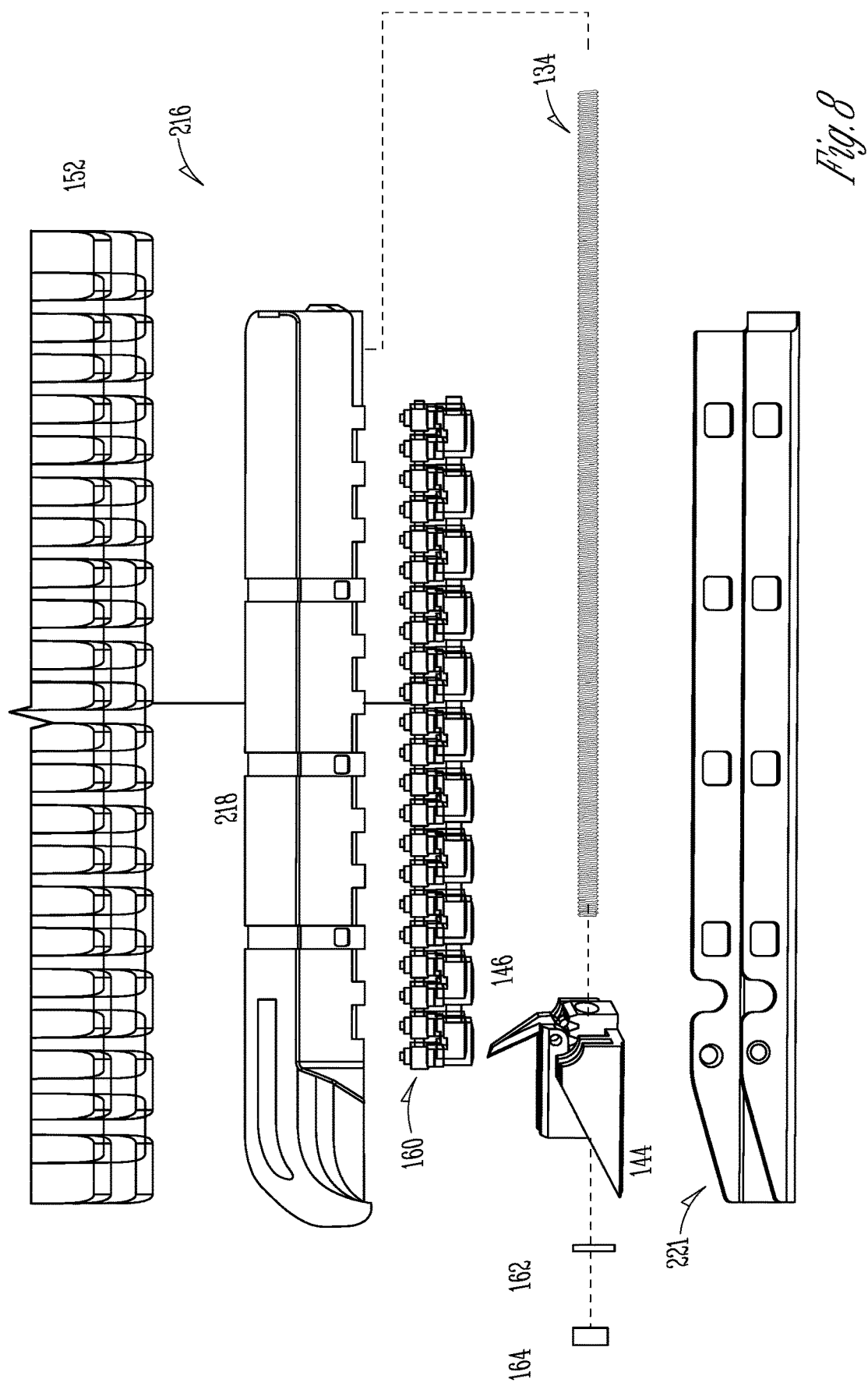

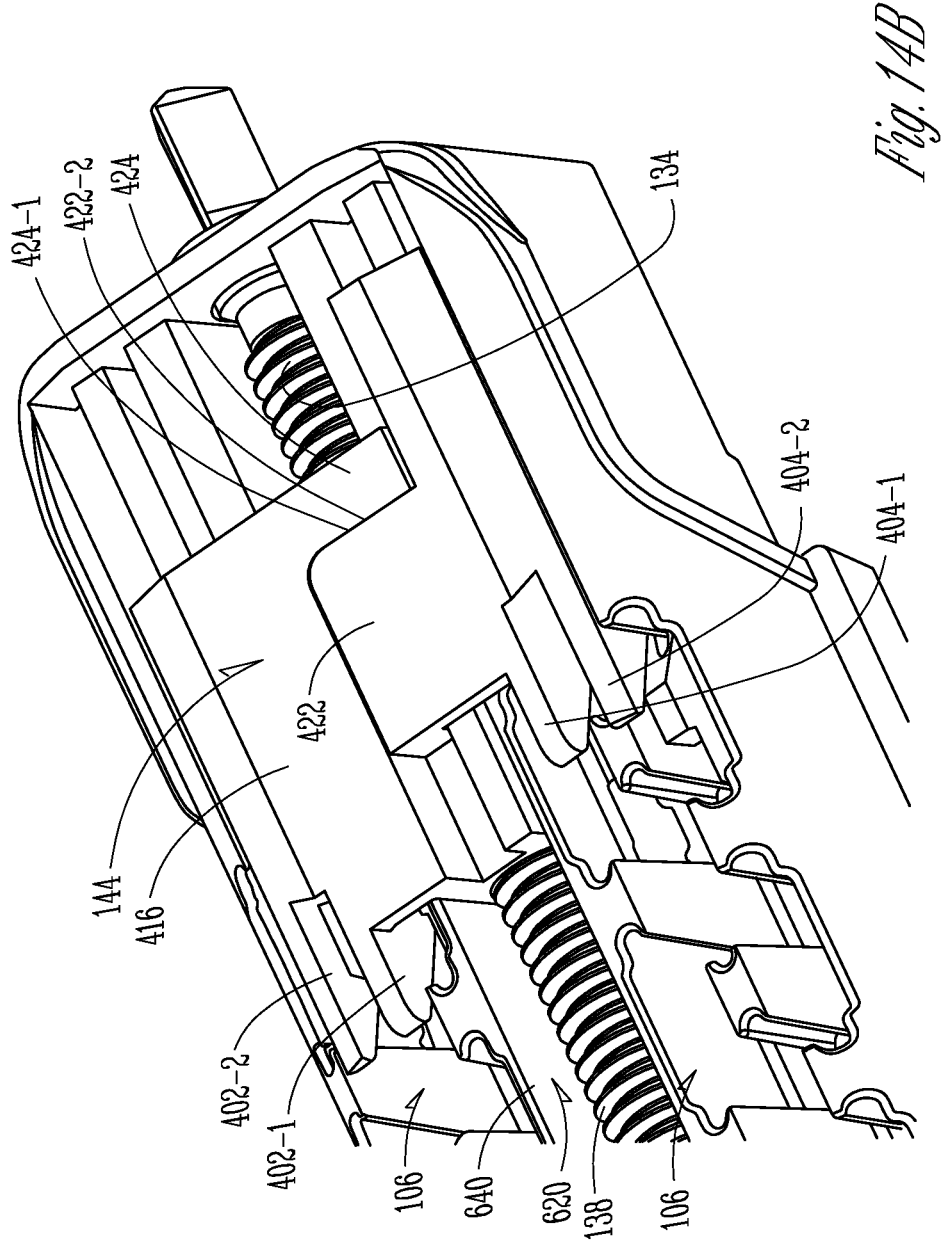

STAPLE PUSHER WITH LOST MOTION BETWEEN RAMPS

RELATED APPLICATIONS

This patent application is a U.S. National Stage Filing under 35 U.S.C. 371 from International Application No. PCT/US2016/059552, filed on Oct. 28, 2016, and published as WO 2017/083126 A1 on May 18, 2017, which claims priority to and the benefit of the filing date of U.S. Provisional Patent Application 62/255,129, entitled "STAPLE PUSHER WITH LOST MOTION BETWEEN RAMPS" filed Nov. 13, 2015, which is incorporated by reference herein in its entirety.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

Minimally invasive teleoperated surgical systems have been developed to increase a surgeon's dexterity when working on an internal surgical site, as well as to allow a surgeon to operate on a patient from a remote location (outside the sterile field). In a teleoperated surgical system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the teleoperated surgical system can provide mechanical actuation and control of a variety of surgical instruments or tools having end effectors that perform various functions for the surgeon, for example, holding or driving a needle, grasping a blood vessel, dissecting tissue, stapling tissue, or the like, in response to manipulation of the master input devices.

SUMMARY

In one aspect, a drive shuttle includes a leader ramp mount that includes a longitudinal first axis. A first leader ramp depends from (i.e. that physically couples to, such as by extending from, being directly attached to, being indirectly attached to through one or more intermediate components, being physically interlocked with, being part of the same component as, physically touching, etc.) a first side of the leader ramp mount. A pusher protrusion depends from a second side of the leader ramp mount. A follower protrusion depends from a follower ramp mount. A first follower ramp depends from the follower protrusion. The first leader ramp, the pusher protrusion, the first follower ramp and the follower protrusion are disposed in relation to each another such that, in the first configuration, the pusher protrusion is spaced apart longitudinally from the follower protrusion by an offset amount and the first leader ramp is aligned longitudinally with the first follower ramp. The first leader ramp, the pusher protrusion, the first follower ramp and the follower protrusion also are disposed in relation to each another such that, in the second configuration, the pusher protrusion contacts the follower protrusion and the first leader ramp is spaced apart longitudinally from the first follower ramp by the offset amount.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7A is an illustrative perspective drawing of a surgical tool assembly with first and second jaws shown in an open position in accordance with some embodiments.

FIG. 8 is an illustrative exploded view of a detachable jaw in accordance with some embodiments.

FIG. 14B is an illustrative drawing showing a bottom perspective view of the drive shuttle seated within the proximal end portion of the cartridge body in the offset configuration described above with reference to FIG. 11D.

DESCRIPTION OF EMBODIMENTS

Figure 1:
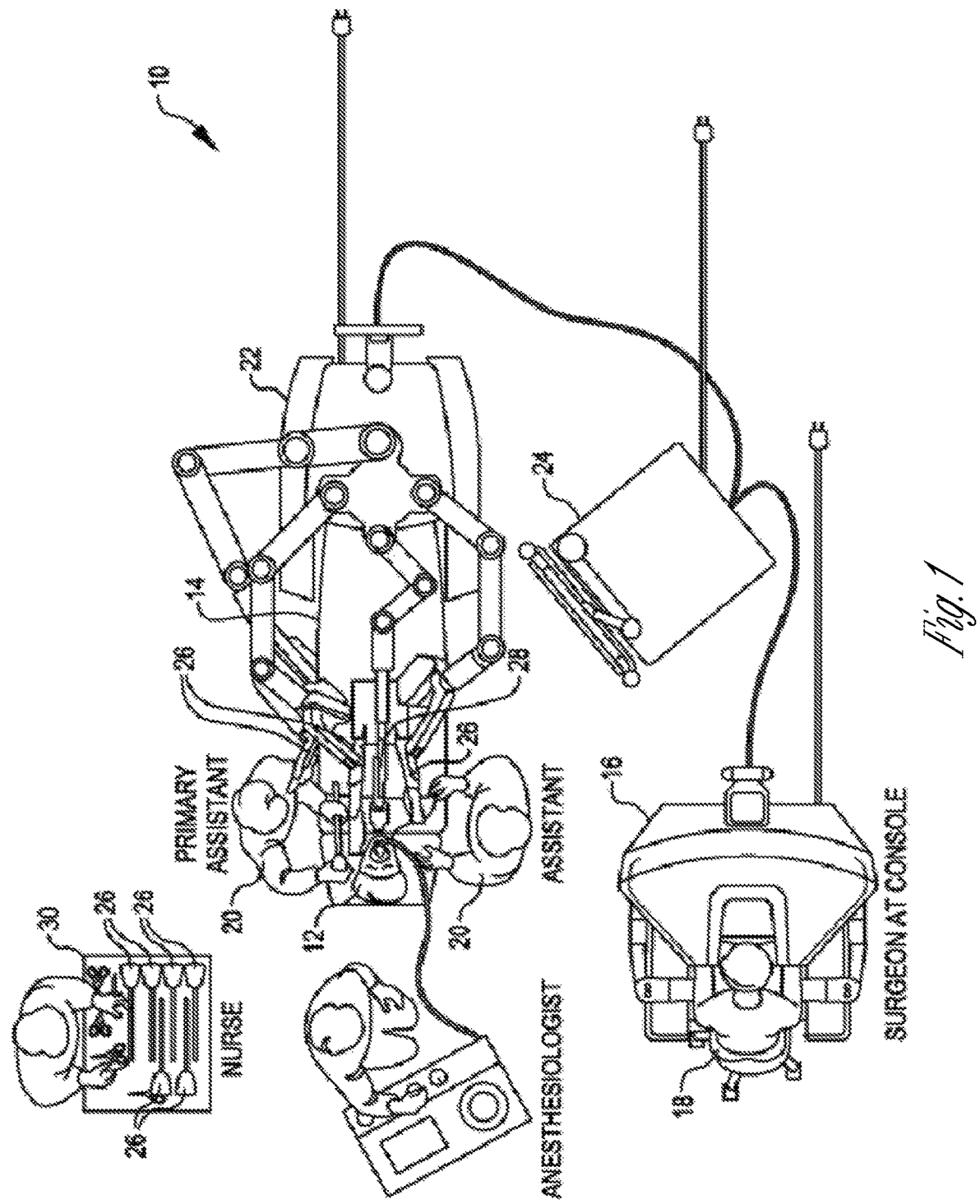
FIG. 1 is an illustrative plan view illustration of a teleoperated surgical system in accordance with some embodiments.

The following description is presented to enable any person skilled in the art to create and use a staple pusher with lost motion between ramps for use in a surgical system. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Referring now to the drawings, in which like reference numerals represent like parts throughout the several views, FIG. 1 is an illustrative plan view of a teleoperated surgical system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The teleoperated surgical system 10 can further include a Patient Side Cart 22 and an Electronics Cart 24. The Patient Side Cart 22 can manipulate at least one removably coupled tool assembly 26 (hereinafter also referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors.

Figure 2:
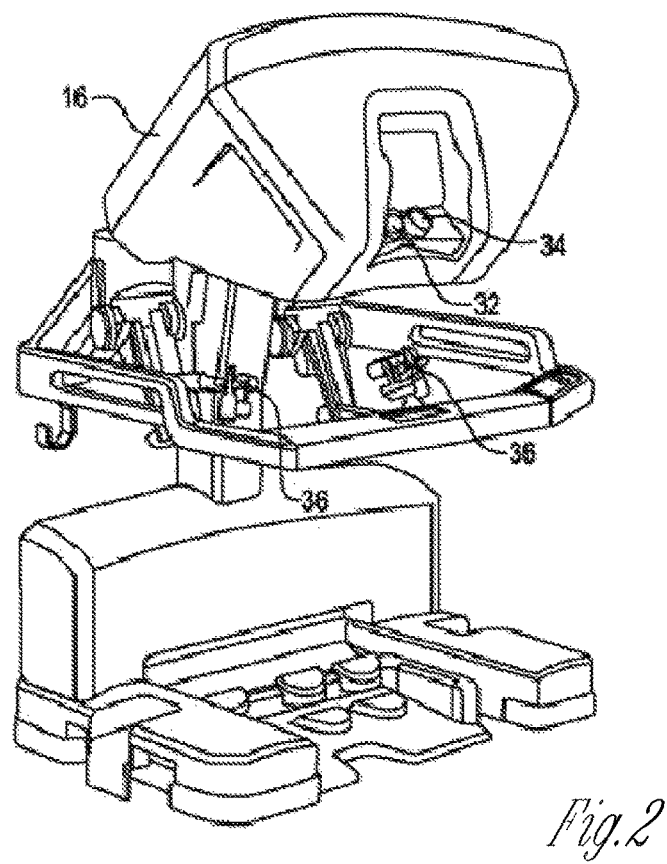
FIG. 2 is an illustrative perspective view of the Surgeon's Console in accordance with some embodiments.

FIG. 2 is an illustrative perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

Figure 3:
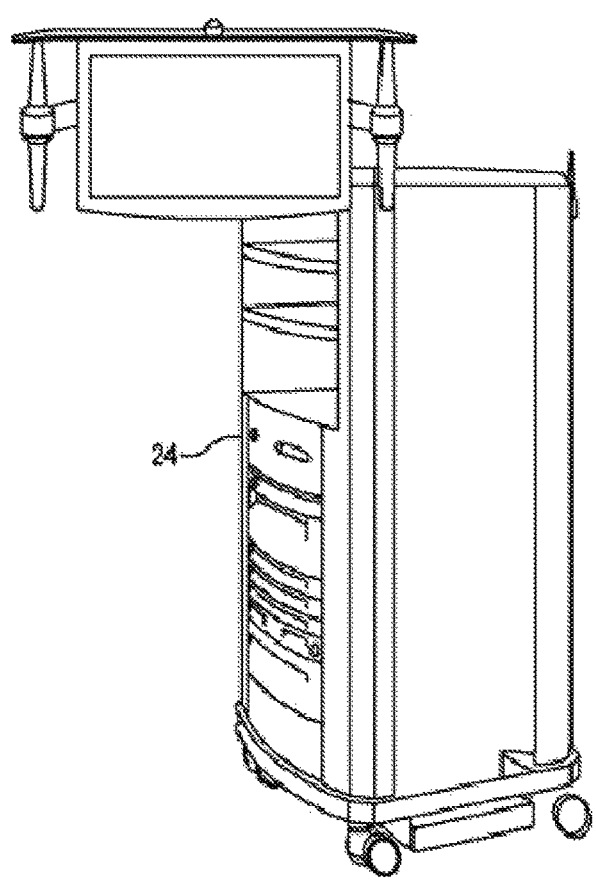
FIG. 3 is an illustrative perspective view of the Electronics Cart in accordance with some embodiments.

FIG. 3 is an illustrative perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope.

Figure 4:
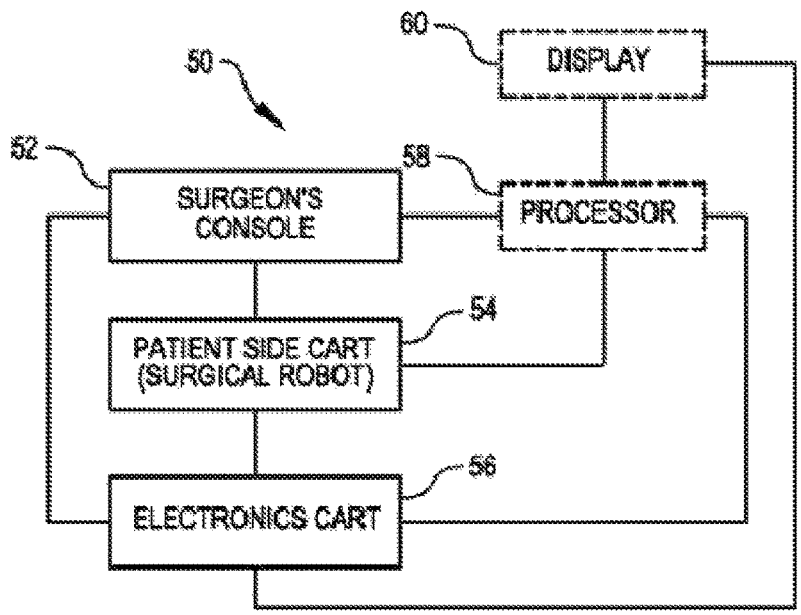
FIG. 4 is an illustrative bock diagram diagrammatically representing functional relationships among components of a teleoperated surgery system in accordance with some embodiments.

FIG. 4 is an illustrative bock diagram diagrammatically representing functional relationships among components of a teleoperated surgery system 50 (such as system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
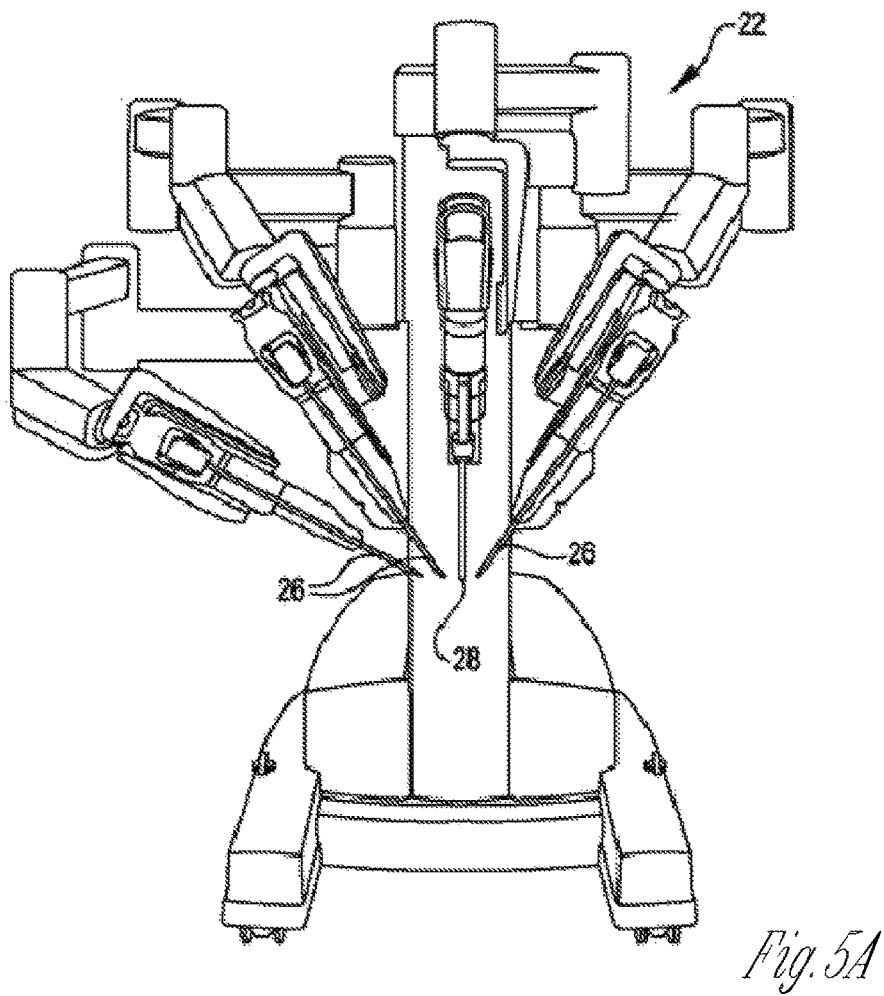
FIGS. 5A-5B are illustrative drawings showing a Patient Side Cart and a surgical tool 62, respectively in accordance with some embodiments.
Figure 5B:
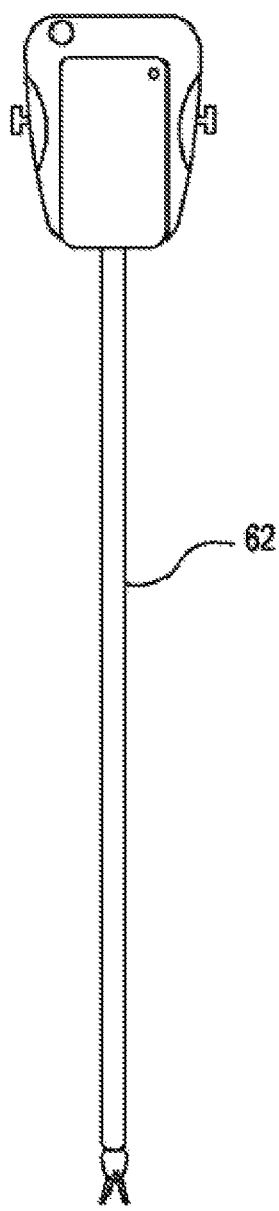

FIGS. 5A-5B are illustrative drawings showing a Patient Side Cart 22 and a surgical tool 62, respectively in accordance with some embodiments. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by teleoperated mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Figure 6:
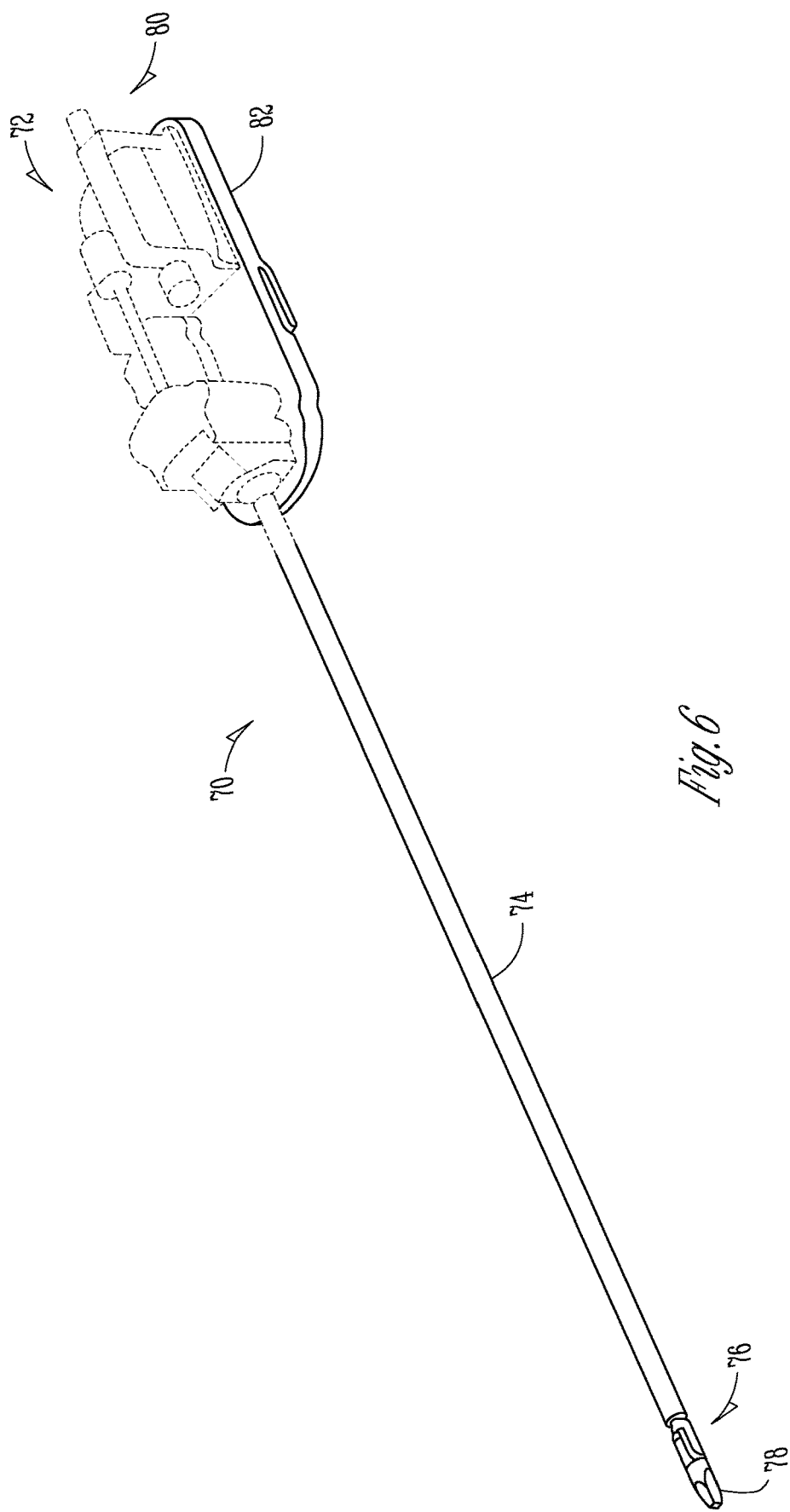
FIG. 6 is an illustrative drawing showing an example surgical tool in accordance with some embodiments.

FIG. 6 is an illustrative drawing showing an example surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Figure 7B:
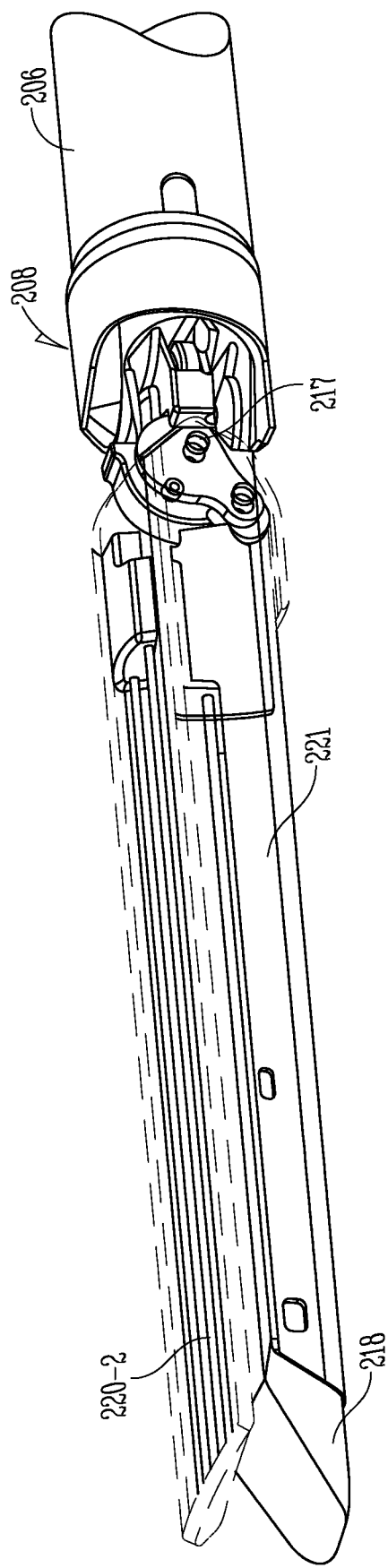
FIG. 7B is an illustrative side view of the distal portion of the surgical tool assembly of FIG. 7A, enlarged to show additional details in accordance with some embodiments.

FIG. 7A is an illustrative perspective drawing of a surgical tool assembly 200 with first and second jaws 214, 216 shown in an open position in accordance with some embodiments. The tool assembly 200 includes a proximal actuation assembly 202, a main shaft 206, a two degree of freedom (2-dof) wrist 208, shown in partial cutaway, and an end effector 210. The end effector 210 includes an end effector base 212 coupled to a distal side of the 2-dof wrist 208, a first articulable jaw 214 and a detachable stationary second jaw 216. The first jaw 214 has a distal end 214-1 and a proximal end 214-2. The second jaw 216 also has a distal end 216-1 and a proximal end 216-2. The end effector base 212 includes a pivot pin 217 secured between the end effector base 212 and a proximal end of the first jaw 214, about which a proximal end of the first jaw 214 pivots to achieve opening and closing movement of the first jaw 214 relative to the second jaw 216. In an open position shown in FIG. 7A, the first jaw 214 is rotated to a position in which distal ends 214-1, 216-1 of the first and second jaws 214, 216 are spaced apart so that the jaws can be more easily maneuvered within a surgical site to encompass anatomical tissue (not shown) between them without actually clamping the tissue in place between them.

In many embodiments, the actuation assembly 202 is operatively coupled with the wrist 208 so as to selectively reorient the end effector 210 relative to the main shaft 206 in two dimensions, referred to as pitch and yaw, and is operatively coupled with the end effector 210 so as to actuate one or more end effector features, such as rotation of the first jaw 214 about the pivot pin 217 to open and close the first jaw 214 relative to the end effector base 212 and the second jaw 216. In accordance with some embodiments, control cables (not shown) extend through a bore in the main shaft 206 to interconnect the actuation assembly 202 with the wrist 208. The actuation assembly 202 imparts forces to the control cables that result in pitch and yaw movement of the wrist 208 and the end effector 210. Details of a suitable cable control mechanisms that can be used are disclosed in U.S. Pat. No. 8,852,174 (filed Nov. 12, 2010) issued to Burbank, which is expressly incorporated herein in its entirety by this reference. In accordance with some embodiments a rotationally-driven clamping mechanism (not shown) actuates the upper jaw 214 relative to the lower jaw 216 to securely clamp tissue between the upper and lower jaws. The clamping mechanism is rotationally driven by a drive shaft (not shown) disposed internal to the main shaft 206. Details of a suitable drive shaft-driven clamping mechanism that can be used are disclosed in U.S. Pat. No. 8,876,857 issued to Burbank (filed Nov. 12, 2010), the full disclosure of which is hereby expressly incorporated herein by reference. In alternative embodiments, suitable cables (not shown) are used to impart forces to open or close the jaws 214, 216.

Figure 7C:
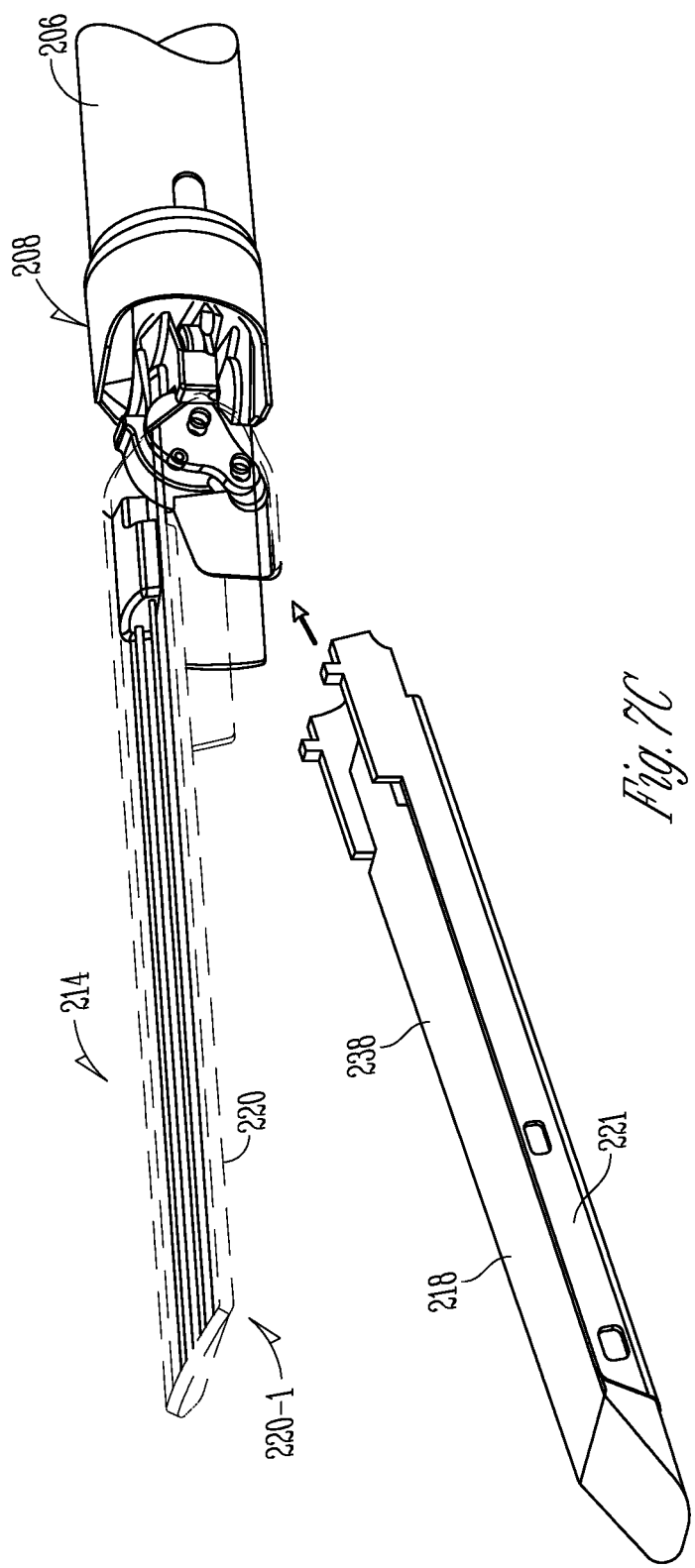
FIG. 7C is an illustrative perspective view of an end effector of the surgical tool assembly of FIGS. 7A-7B that includes first and second jaws with a detachable stationary second jaw shown detached from the rest of the end effector, in accordance with some embodiments.

The end effector 210 includes a surgical stapler in which the second jaw 216 is detachable and stationary relative to the base 212. In a closed position shown in FIG. 7B, the first and second jaws are disposed parallel to each other spaced apart by an amount to accommodate anatomical tissue (not shown) that may be clamped between them. The first jaw 214 includes an anvil 220 having an anvil surface 220-1 that faces the second jaw 216. In operation, staples are deformed against the anvil surface 220-1 to staple together tissue (not shown) disposed between the first and second jaws 214, 216. The second jaw 216 includes an elongated stapler cartridge body 218 seated within a stapler cartridge body support channel 221 configured to support the cartridge body 218. The stapler cartridge body 218 carries fasteners, e.g., staples to be used to attach tissue during a surgical procedure. The stapler cartridge body 218 defines a central longitudinal knife slot 238 that extends through the cartridge body 218 and extends along substantially its entire length. The stapler cartridge body 218 also defines multiple laterally spaced rows of staple openings 106 that each extends longitudinally along the cartridge body 218. In some embodiments, three rows of staple openings 106 extended along one side of the knife slot 238, and three rows of staple openings extended along an opposite side of the knife slot 238. Each staple retention slot 240 is sized to receive a staple 242. FIG. 7C shows the second jaw 216 detached from the base portion 212 of the end effector 210. In operation, the second jaw 216 containing a full load of staples is releasably secured to cooperate with the first anvil surface 220-1, facing the second jaw 216, so as to deform staples so as to fasten them to staple anatomical tissue (not shown) disposed between the jaws when they are in a closed position. Once the staples have been fired, the second jaw 216 with the spent cartridge body 218 can be removed and may be replaced by a replacement second jaw 216 with a fully loaded stapler cartridge body 218.

FIG. 8 is an illustrative exploded view of a detachable stationary second jaw 216 in accordance with some embodiments. The second jaw 216 includes the cartridge body 218, staples 152, staple pushers 160, a drive shuttle 144, a knife 146, a lead screw 134, a thrust washer 162, a lead screw nut 164, and a cartridge body support channel 221. The cartridge body 218 includes a distal end portion 238-1 and a proximal end portion 238-2. The cartridge body 218 defines the staple openings 106 arranged in six rows, with three rows of the staple openings 106 being disposed on each side of the longitudinal knife slot 238. The staple pushers 160 interface with the staples 152 and slidingly interface with the cartridge body 218. Motion of the drive shuttle 144 along the threaded portion 135 of the lead screw 134 results in engagement of the staple pushers 160 by distally-facing ramp surfaces 176 of the first drive shuttle 144 to drive the staple pushers 160 up relative to the cartridge body 218, toward the anvil face 220-1, to deploy the staples 152 as the drive shuttle 144 moves towards the distal end 218-1 of the cartridge body 218. In some embodiments, the knife 146 is pivotally supported from the drive shuttle 144.

The components of the second jaw 216 can be assembled using the following assembly sequence. First, with the cartridge body 218 in a "bottom up" orientation, the staple pushers 160 are installed into the staple openings 106. Next, the drive shuttle 144, the knife 146 pivotally supported from the drive shuttle 144, the thrust washer 162, and the lead screw nut 164 are installed onto the lead screw 134 and the lead screw nut 164 is laser welded flush to the end of the lead screw 134. The resulting lead screw assembly is then installed into the cartridge body 218 with the drive shuttle 144 at a proximal end of the cartridge body 218-2 and at a proximal end of the lead screw 134 with the knife 146 secured to the drive shuttle 144 for use to cut tissue as the drive shuttle 144 is advanced in a distal direction along the length of the cartridge body 218. The staples 152 are installed into the staple openings 106. Additional details of components and assembly of a suitable second jaw 216 that can be used are disclosed in U.S. Pat. No. 8,991,678 issued to Wellman et al. (filed Oct. 26, 2012), the full disclosure of which is hereby expressly incorporated herein by reference.

In an alternative embodiment, described in patent application No. 62/255,123, filed on Nov. 13, 2015 and entitled "Stapler with composite cardan and screw drive," which is expressly incorporated herein in its entirety by this reference, the drive shuttle 144 has an "I-beam" configuration, and cables (not shown) are configured to drive the drive shuttle 144 along the length of the cartridge body 218. A cable attached to a top of the drive shuttle 144 pulls it in the distal direction. A second cable attached to a lower portion of the drive shuttle 144 pulls it in the proximal direction.

Figure 9A:
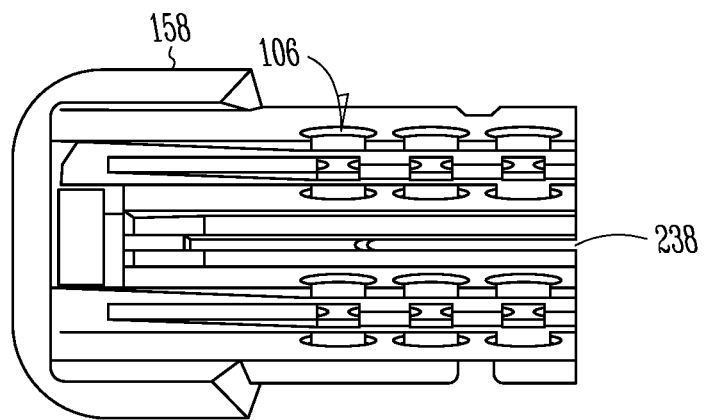
FIG. 9A is an illustrative top elevation view of a distal end portion of the cartridge body in accordance with some embodiments.
Figure 9B:
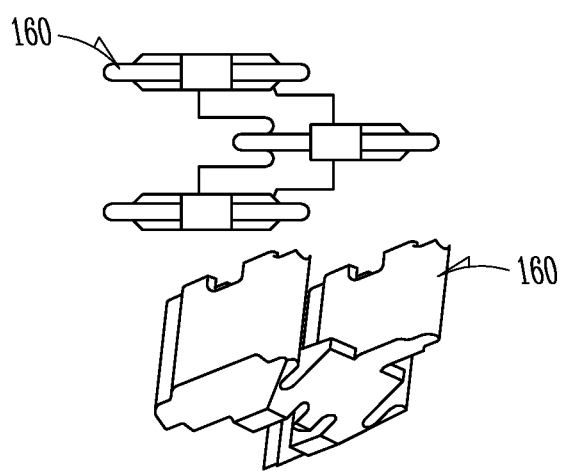
FIG. 9B is an illustrative top view and an illustrative perspective view of a staple pusher for use with the cartridge body of FIG. 9B in accordance with some embodiments.

FIG. 9A is an illustrative top elevation view of a distal end portion 218-2 of the cartridge body 218 in accordance with some embodiments. FIG. 9B is an illustrative top view and an illustrative perspective view of a staple pusher 160 in accordance with some embodiments. As illustrated, the staple openings 106 and the staple pushers 160 have complementary shapes such that each of the staple pushers 160 is accommodated within one of the staple openings 106 for translation within the staple opening 106 in response to being driven by the drive shuttle 144 as the drive shuttle 144 is translated longitudinally along the length of the cartridge body 218 from its proximal end 218-2 toward its distal end 218-1.

Figure 10:
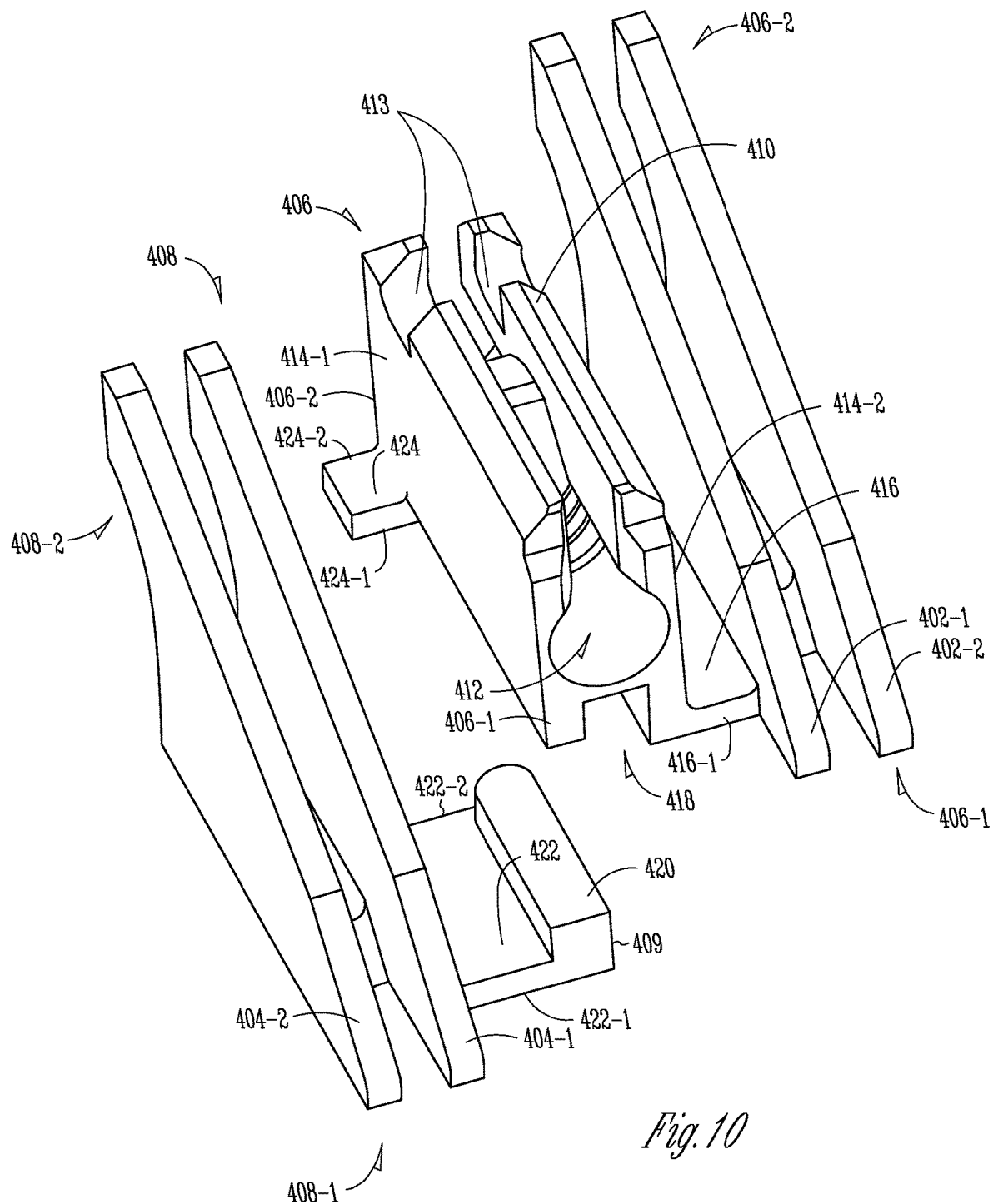
FIG. 10 is an illustrative front perspective exploded view of the drive shuttle in accordance with some embodiments.

FIG. 10 is an illustrative front perspective exploded view of the drive shuttle 144 in accordance with some embodiments. The drive shuttle 144 includes two major parts that are moveable relative to one another: a leader member 406 and a follower ramp member 408. The leader member 406 includes first and second leader ramps 402-1, 402-1. The follower member 408 includes first and second follower ramps 404-1, 404-2.

The leader member 406 includes a distal portion 406-1, also referred to herein as a front side, and a proximal portion 406-2, also referred to herein as a back side. The leader member 406 includes a leader ramp mount 410 that defines a longitudinal screw bore 412 that includes internal threads to engage the lead screw 134. The leader ramp mount 410 has a leader ramp side 414-1, also referred to herein as a second lateral side, facing toward the first and second leader ramps 402-1, 402-2 and has a follower ramp side 414-2, also referred to herein as a first lateral side, facing toward the first and second follower ramps 404-1, 404-2. An integral leader side spacer beam 416 extends transversely outward in a first direction from the leader ramp side 414-1 of the leader ramp mount 410. The leader side spacer beam 416 includes a distal edge (of the distal surface) 416-1 and a proximal edge (of the proximal surface) 416-2. The first and second leader ramps 402-1, 402-2 extend from the leader side spacer beam 416, which has a width selected to space them apart transversely from the lead screw engagement member 406 and to align them with rows of staple openings that are pushed by the first and second leader ramps 402-1, 402-2. The leader ramp mount 410 defines a central longitudinal slot 418 that acts as a first guide component and that extends parallel to and beneath the screw bore 412. The leader ramp mount 410 also includes knife mount bearing surfaces 413 to rotatably mount the knife 146.

The follower member 408 includes a distal portion 408-1 and a proximal portion 408-2. The follower member 408 includes a follower ramp mount 409 that includes an upstanding guide rail 420 that acts as a second guide component. The guide rail 420 has a surface that is complementary to a surface of the slot 418 in that it is sized to slidably interfit with the slot 418. The slot 418 and the rail 420 cooperate to fix the transverse alignment of the leader ramp mount 410 with the follower ramp mount 409 (e.g., perpendicular to the lead screw longitudinal axis) while permitting them to change their longitudinal alignment with each other. The rail 420 has a length is shorter than a length of the slot 418 and can slide longitudinally within the slot 418. An integral follower protrusion 422 extends transversely between the follower ramp mount 409 and the first and second follower ramps 404-1, 404-2. In some embodiments, the follower protrusion 422 includes a follower beam that extends transversely between the follower ramp mount 409 and the first and second follower ramps 404-1, 404-2. The follower protrusion 422 includes a distal edge (of the distal surface) 422-1 and a proximal edge portion (of the proximal surface) 422-2. The first and second follower ramps 404-1, 404-2 extend from the follower protrusion 422, which has a width selected to space them apart transversely from the lead screw engagement member 406, when the rail 420 is received within the slot 418 and to align them with rows of staple openings that are pushed by the first and second leader ramps 402-1, 402-2.

An integral follower pusher protrusion 424 extends transversely outward from a proximal portion of the leader ramp mount 410 in a second direction, generally opposite to the direction in which the leader side spacer beam 416 extends, from its leader ramp side 414-1. In some embodiments, the pusher beam 424 includes a beam that extends transversely outward from a proximal portion of the leader ramp mount 410 in the second direction. The pusher protrusion 424 includes a distal edge 424-1 and a proximal edge 424-2. The distal edge 424-1 of the pusher protrusion 424 is disposed aligned with and facing the proximal edge portion 422-2 of the follower protrusion 422 when the rail 420 is received within the slot 418. Through actuation of the rotation lead screw 134, while the rail 420 is received within the slot 418, the leader member 406 can be slidably moved relative to the follower member 408 so as to bring the distal edge 424-1 of the pusher protrusion 424 to contact the proximal edge portion 422-2 of the follower protrusion 422. In operation, when the lead screw imparts a longitudinal translation force to the leader member 406 and the pusher protrusion 424 contacts the follower protrusion 422, the pusher protrusion 424 imparts the translation force to the follower protrusion 422, causing the follower ramp member 408 to follow the motion of the leader member 406.

Figure 11A:
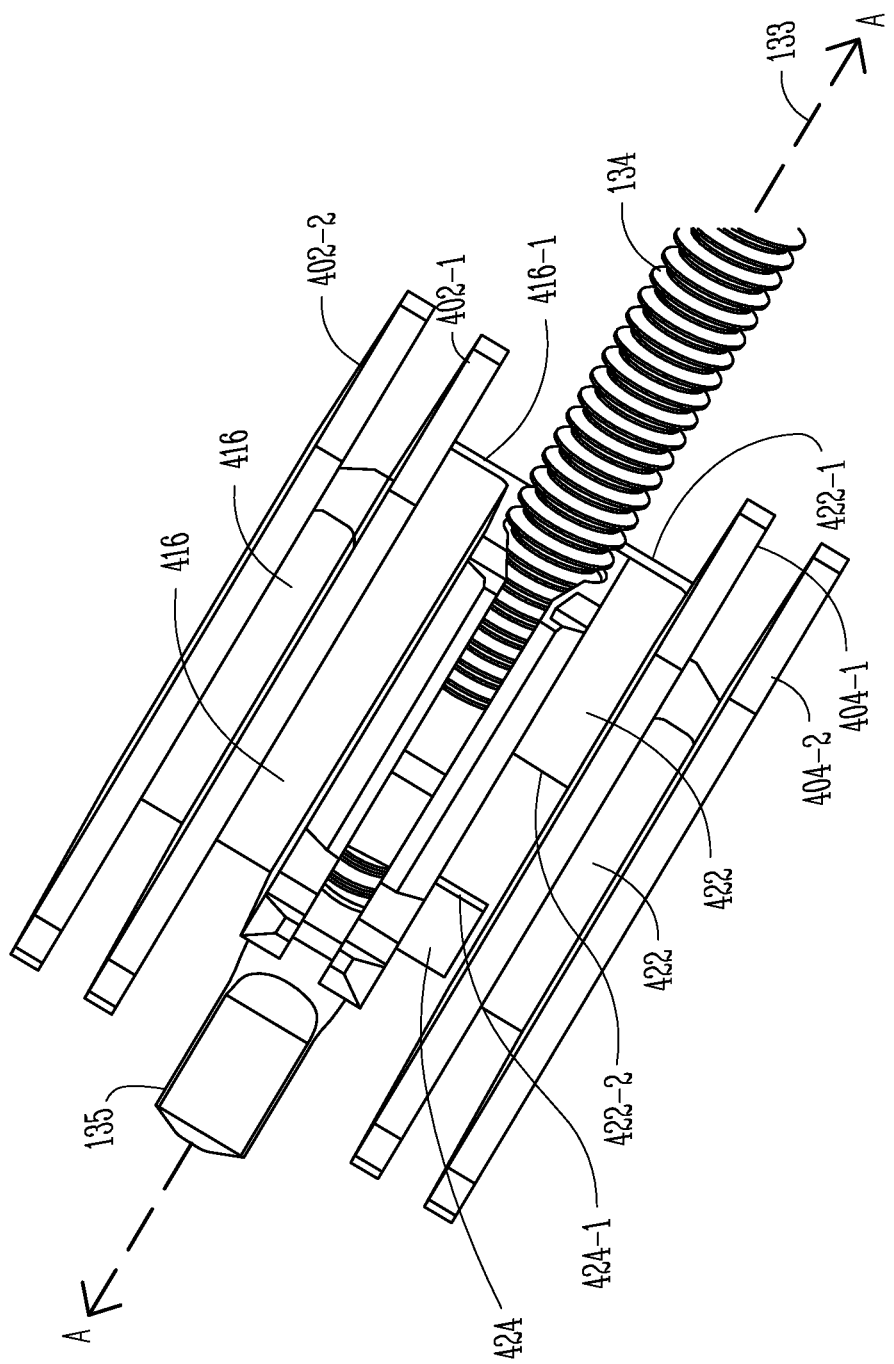
FIG. 11A is an illustrative top elevation view of the drive shuttle fully assembled showing the leader ramps and follower ramps longitudinally aligned in accordance with some embodiments.
Figure 11B:
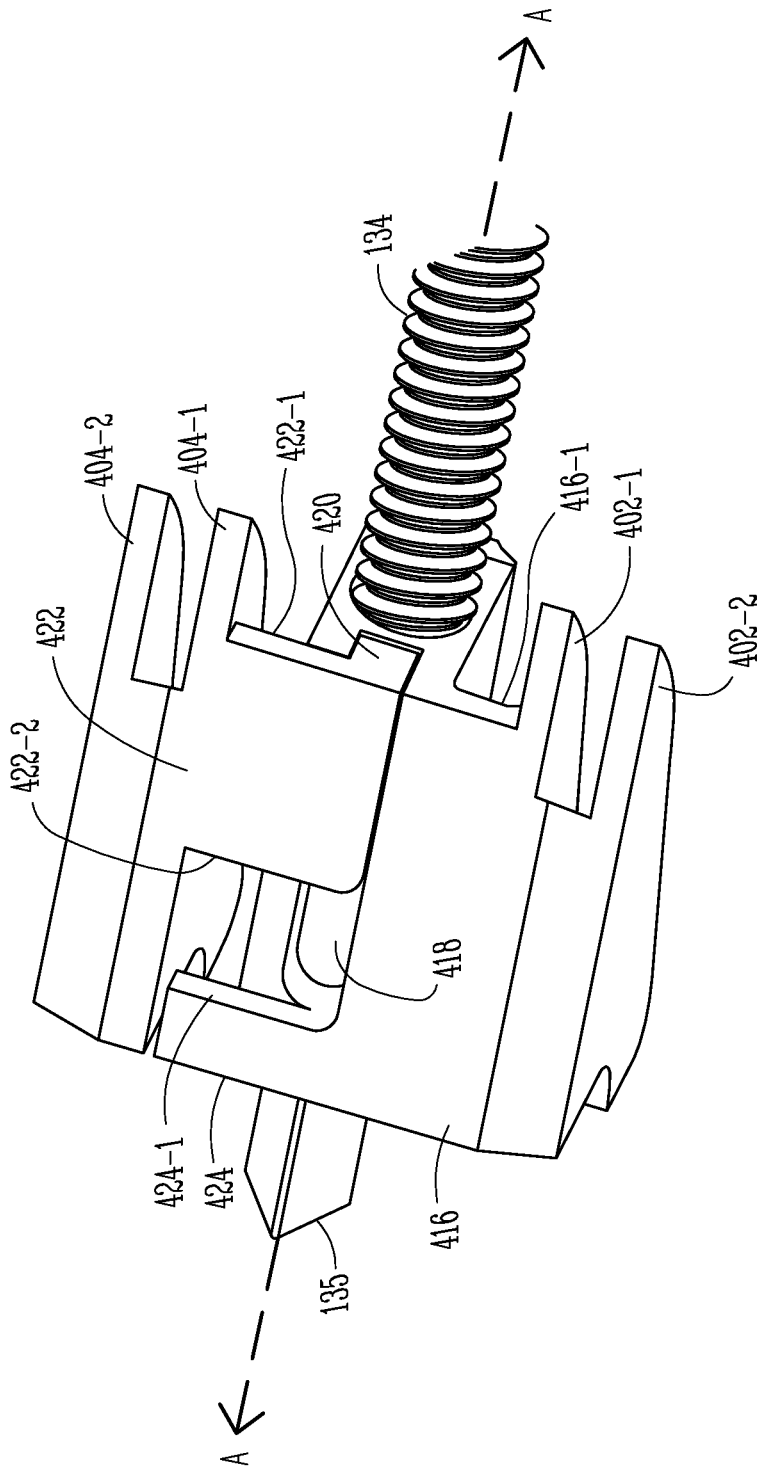
FIG. 11B is an illustrative bottom perspective view of the drive shuttle fully assembled showing the leader ramps and follower ramps longitudinally aligned in accordance with some embodiments.

FIG. 11A is an illustrative top elevation view of the drive shuttle 144 fully assembled showing the leader ramps 402-1, 402-2 and follower ramps 404-1, 404-2 longitudinally aligned with a first axis (A-A) 133 in accordance with some embodiments. FIG. 11B is an illustrative bottom perspective view of the drive shuttle 144 fully assembled showing the leader ramps 402-1, 402-2 and follower ramps 404-1, 404-2 longitudinally aligned in accordance with some embodiments. More particularly, the rail 420 is disposed in a starting position within the slot 418, in accordance with some embodiments, such that the distal edge 416-1 of the leader side spacer beam 416 is longitudinally aligned with the distal edge 422-1 of the follower protrusion 422. Moreover, with the rail 420 disposed in the starting position within the slot 418, the proximal edge portion 422-2 of the follower protrusion 422 is longitudinally spaced apart from the distal edge 424-1 of the pusher protrusion 424, in a direction parallel to the axis of the drive screw 134, by a prescribed distance referred to herein as a 'lost motion' distance.

Figure 11C:
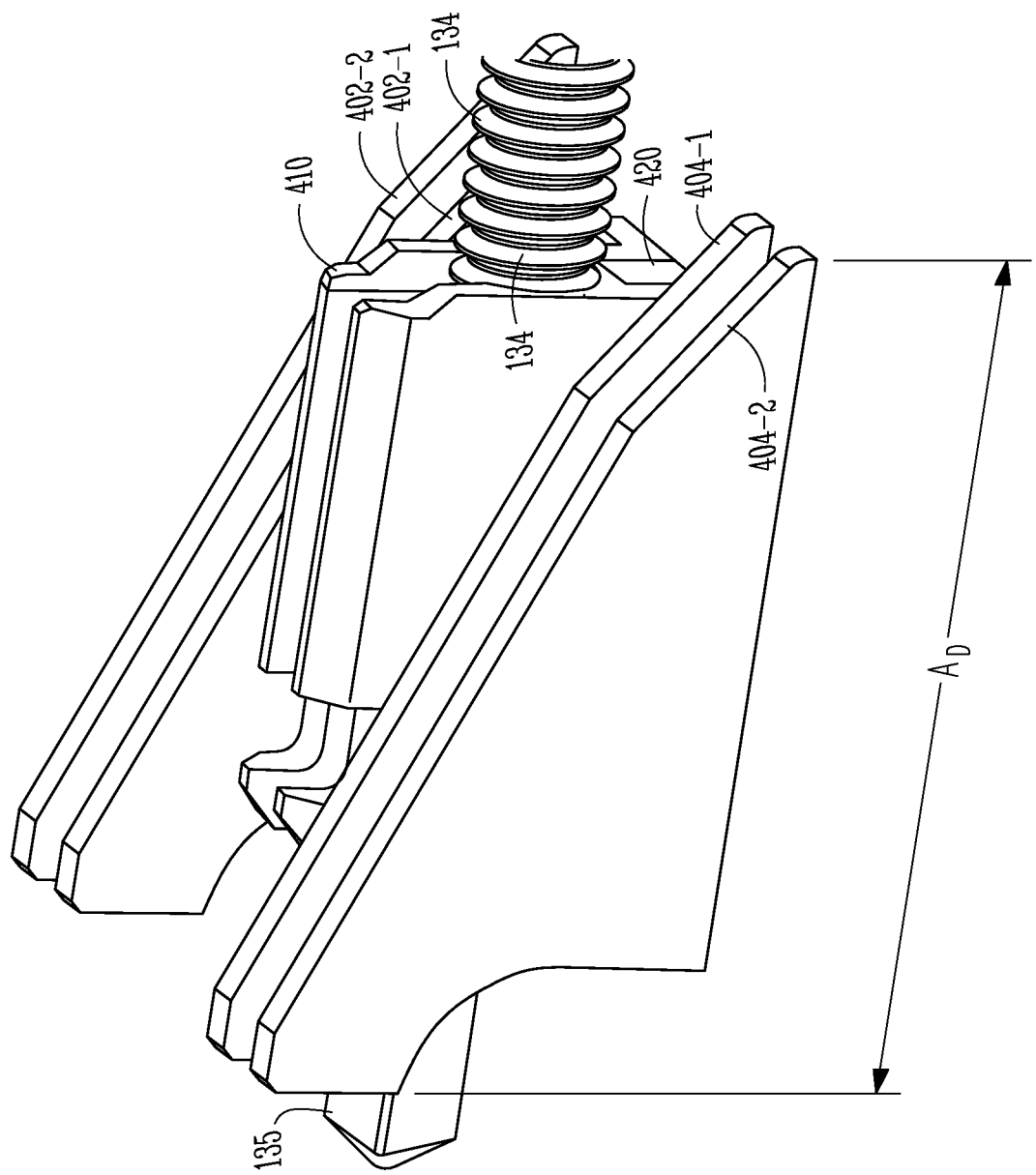
FIG. 11C is an illustrative front side perspective view of the drive shuttle configured with the leader ramps and follower ramps longitudinally aligned in accordance with some embodiments.
Figure 11D:
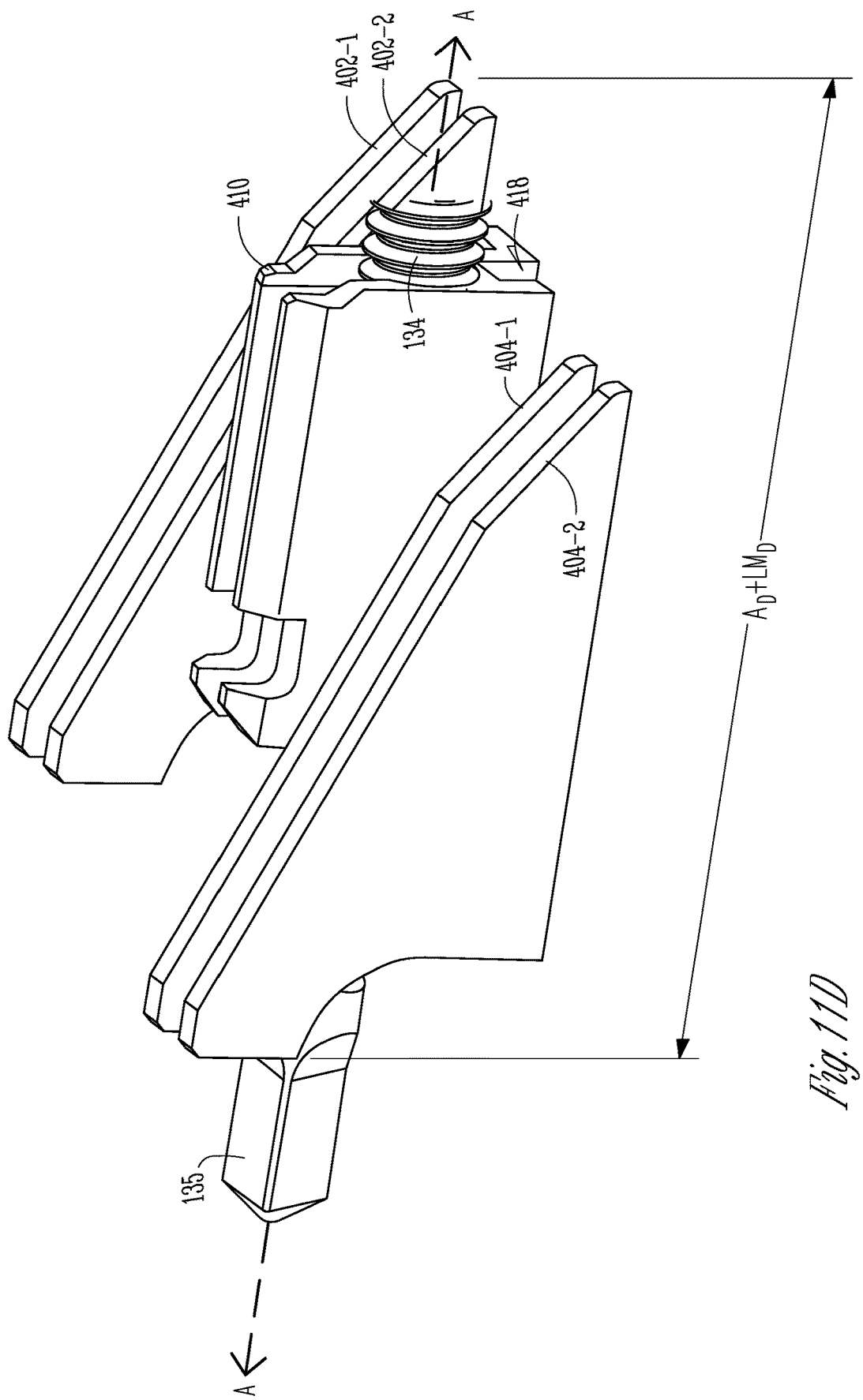
FIG. 11D is an illustrative front side perspective view of the drive shuttle configured with the leader ramps leading the follower ramps in accordance with some embodiments.

FIG. 11C is an illustrative front side perspective view of the drive shuttle 144 configured with the leader ramps 402-1, 402-1 and follower ramps 404-1, 404-2 longitudinally aligned in a first configuration in accordance with some embodiments. FIG. 11D is an illustrative front side perspective view of the drive shuttle 144 configured with the leader ramps 402-1, 402-1 leading the follower ramps 404-1, 404-2 by an offset amount in a second configuration in accordance with some embodiments. In the longitudinally aligned configuration, also referred to herein as the first configuration, shown in FIG. 11C, an overall length of the drive shuttle from the distal tips of the aligned first and second leader ramps 402-1, 402-1 and first and second follower ramps 404-1, 404-2 to the most extreme proximal portion of the drive shuttle is $A_D$. However, in longitudinally displaced configuration, also referred to herein as the first configuration, in which the first and second leader ramps 402-1, 402-1 are longitudinally displaced by an offset amount from the first and second follower ramps 404-1, 404-2, and the overall length is $A_D = LM_D$. The offset amount is determined by a distance $LM_D$, referred to herein as a "lost motion" distance, which is the distance between the proximal edge portion 422-2 of the follower protrusion 422 and the distal edge 424-1 of the pusher protrusion 424 when the distal tips of the leader ramps 402-1, 402-1 are aligned with the distal tips of the follower ramps 404-1, 404-2.

During operation, before staple driving begins, the drive shuttle 144 is initially disposed at a proximal end 218-2 of the cartridge body 218 and is configured with the leader ramps 402-1, 402-1 and follower ramps 404-1, 404-2 longitudinally aligned as shown in FIG. 11C so as to reduce its overall length, i.e. to $A_D$. An advantage of using this initial configuration, in which the shuttle 144 is compacted to $A_D$, is that the overall reload length and distal portion of the stapler can be shortened by the distance $LM_D$. During actual delivery of staples, while the drive shuttle 144 moves longitudinally within the cartridge body 218, it is configured with the leader ramps 402-1, 402-1 leading the follower ramps 404-1, 404-2 by the offset amount, $LM_D$, as shown in FIG. 11D. As explained more fully below, an advantage of this offset is that fewer staples 152 are simultaneously deformed against the anvil face 221-1, resulting in less torque force applied within the end effector 210. More specifically, in the offset configuration, the leader ramps and the follower ramps alternate in causing staple deformation. Thus, only staples 152 from the rows of staples pushed by the leader ramps or rows of staples pushed by the follower actually undergo deformation at any given time, thereby reducing torque forces.

In operation, the shuttle beam starts out in the aligned configuration shown in FIG. 11C. The proximal actuation assembly 202 imparts a rotational force to a coupling member portion 135 of the lead screw 134 causing it to rotate so as to impart a longitudinal translation force to the leader ramp mount 410 portion of the leader member 406. Initially, as the lead screw 134 rotates and imparts a translation motion to the leader member 406, the follower member 408 remains stationary. The interaction of the guide slot 418 and the guide 420 directs relative movement between the leader member 406 the follower member 408 so as to cause the pusher protrusion 424, which moves in concert with the leader member 406, to traverse the lost motion distance that separates it from the follower protrusion 422. Upon traversing the lost motion distance, the pusher protrusion 424 makes contact with the follower protrusion 422 and imparts a force to it causing the follower member 408 to follow the translation movement of the leader member 406, albeit following by the lost motion amount.

Figure 12A:
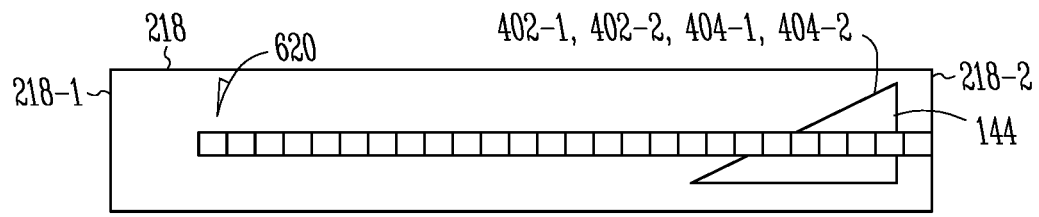
FIGS. 12A-12C are illustrative drawings representing relative positions of the leading ramps and following ramps during different stages of staple deployment process in accordance with some embodiments.
Figure 12B:
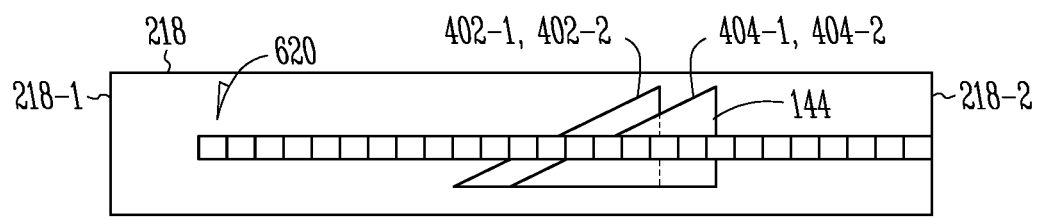
Figure 12C:
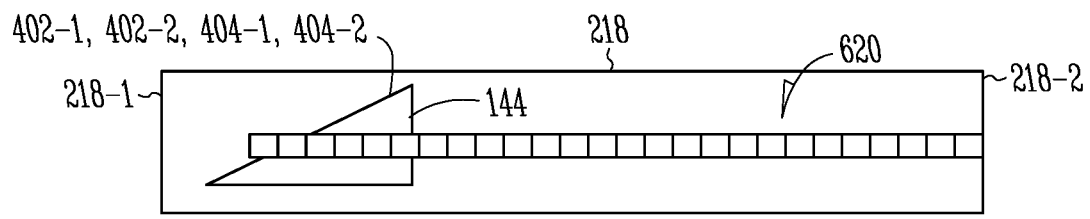

FIGS. 12A-6C are illustrative drawings representing relative positions of the leading ramps and following ramps during different stages of staple deployment process in accordance with some embodiments. The cartridge body 218 defines an internal central cavity 620 extending between its distal end 218-1 and its proximal end 218-2. The lead screw 134 is mounted within the cavity in engagement with the drive shuttle 144 for rotation relative to the housing cartridge body 218 and extends between the distal end 218-1 and its proximal end 218-2 through the central cavity 620. FIG. 12A shows the drive shuttle 144 disposed adjacent the proximal end 218-2 of the cartridge body 218, in a starting configuration with the leader and follower ramps aligned. FIG. 12B shows the drive shuttle 144 disposed in a middle portion of the cartridge body 218, in a staple dispensing configuration with the leader ramps 402-1, 402-2 leading the follower ramps 404-1, 404-2 by the lost motion distance. As explained above, during operation the leader and follower ramps sequentially contact pushers 160 within the longitudinally spaced stapler openings formed in the cartridge body 218 to cause the pushers 242 to translate vertically within openings 106, and to urge staples 152 within the pushers 160 to deform against the anvil surface 221-1. Meanwhile, the knife 146 (not shown) upstands through the cartridge slot 238 and cuts tissue that has been stapled. FIG. 12C shows the drive shuttle 144 disposed adjacent the distal end 218-2 of the cartridge body 218, in a finished configuration with the leader and follower ramps aligned.

Figure 13:
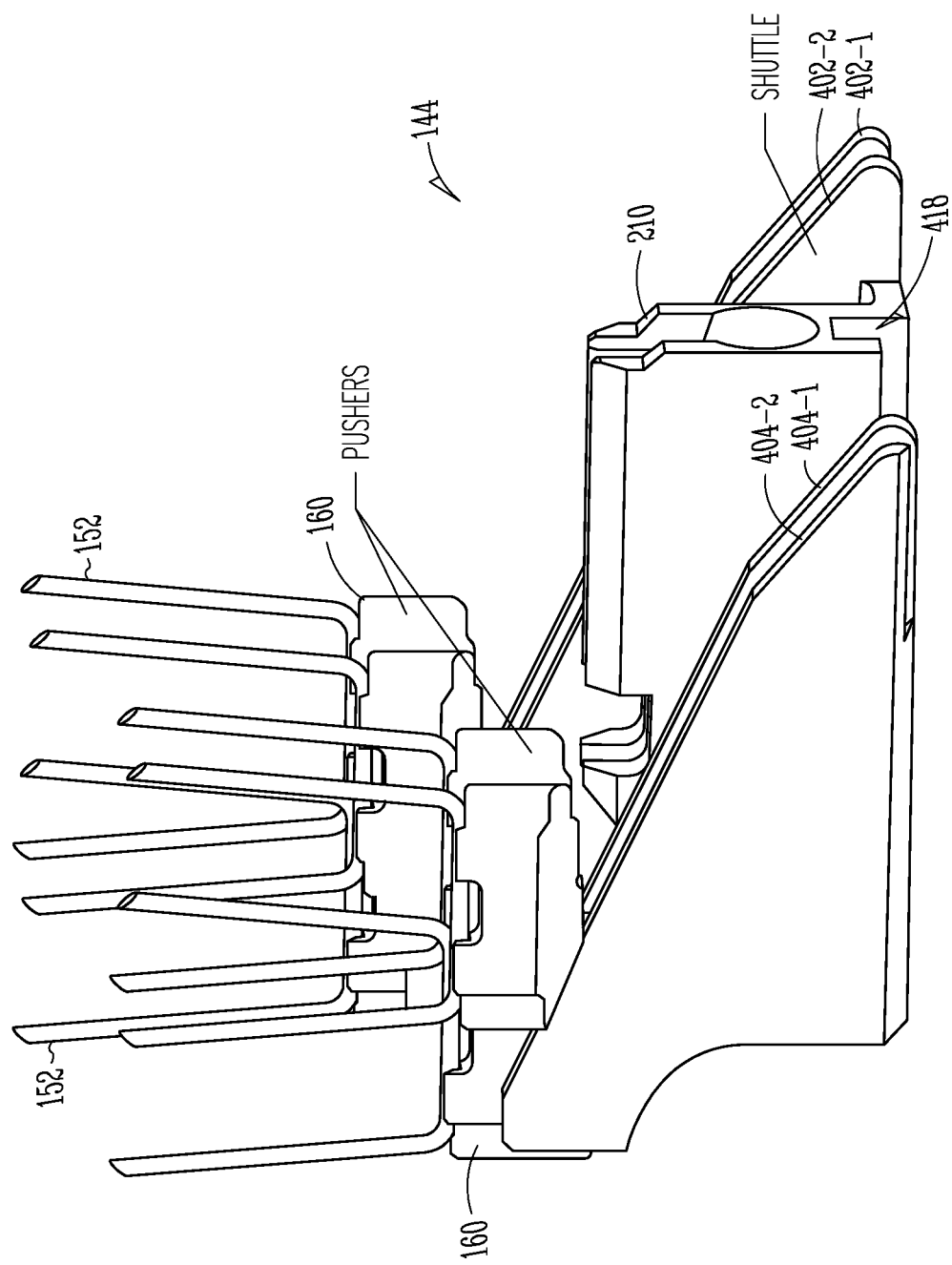
FIG. 13 is an illustrative front perspective view of the drive shuttle in the process of driving pushers and staples held within them in accordance with some embodiments.

FIG. 13 is an illustrative front perspective view of the drive shuttle 144 in the process of driving pushers 160 and staples held within them in accordance with some embodiments. It is noted that the pushers 160 and staples 152 pushed by the first and second leader ramps 402-1, 402-2 have been pushed upward by a greater amount than corresponding pushers and staples pushed by the first and second follower ramps 404-1, 404-2 due to the offset distance between the leader and follower ramps and the fact that the leader ramps 'lead' the follower ramps. It will be appreciated, therefore, that the staples 152 pushed by the first and second leader ramps 402-1, 402-2 will be deformed at a moment in time before the staples 152 pushed by the first and second follower ramps 404-1, 404-2 are deformed. As explained more fully below, the offset in physical spacing between the leader and follower ramps, therefore, results in a time offset between a time at which a torque force is produced due to deformation caused by the leader ramps 402-1, 402-2 and a time at which a torque force is produced due to deformation caused by the follower ramps 404-1, 404-2, thereby reducing instantaneous torque force.

Figure 14A:
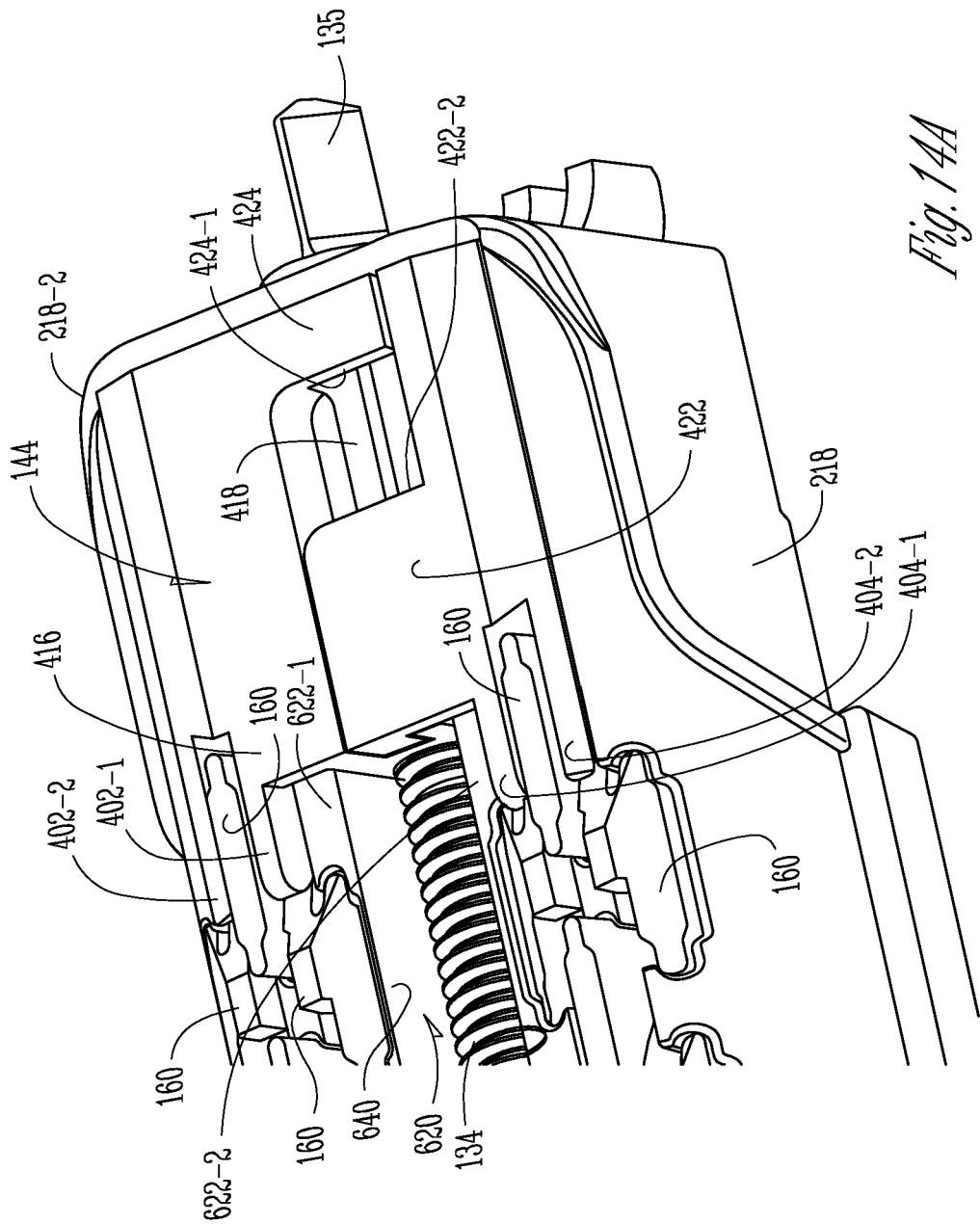
FIG. 14A is an illustrative drawing showing a bottom perspective view of the drive shuttle seated within the proximal end portion of the cartridge body in the aligned configuration described above with reference to FIG. 11C.

FIG. 14A is an illustrative drawing showing a bottom perspective view of the drive shuttle 144 seated within the proximal end portion 218-2 of the cartridge body 218 in the aligned configuration described above with reference to FIG. 11C. The proximal edge portion 422-2 of the follower protrusion 422 is spaced apart from the distal edge 424-1 of the pusher protrusion 424 by the offset amount. Thus, a gap exists between the proximal edge portion 422-2 and the distal edge 424-1. It is noted that a portion of the bottom of the follower member 408 visible within the gap has an outer contour to define the slot 418. The cartridge body 218 defines inner sidewalls 640 that define the cavity 620 in which the lead screw 134 extends and through which the leader ramp mount 410 portion of the drive shuttle 144 moves longitudinally. The cartridge body 218 includes elongated downward facing surfaces 622-1, 622-2 on either side of the cavity 620 in which the stapler openings 106 and in which the staple pushers 160 are inserted. The stapler openings 106 and the staple pushers 160 are situated in groups of three across, laterally, with the middle one of the three being proximally offset longitudinally from the others. The leader side spacer beam 416 slidably contact one of the downward facing surfaces 622-1, and the first and second leader ramps 402-1, 402-1 straddle the proximally offset pusher 160. The first and second leader ramps 402-1, 402-1 upstand within a leader ramp side channel (not shown) defined by the cartridge body 218 in which they travel during traversal from the proximal end 218-2 toward the distal end 218-1 of the cartridge 218 in the course of pushing staples 152 for deformation. Similarly, the follower protrusion 422 slidably contacts the other of the downward facing surfaces 622-2, and the first and second leader ramps 402-1, 402-1 straddle the proximally offset pusher 160. The first and second follower ramps 404-1, 404-1 upstand within a follower ramp side channel (not shown) defined by the cartridge body 218 in which they travel during traversal from the proximal end 218-2 toward the distal end 218-1 of the cartridge 218 in the course of pushing staples 152 for deformation.

FIG. 14B is an illustrative drawing showing a bottom perspective view of the drive shuttle 144 seated within the proximal end portion 218-2 of the cartridge body 218 in the offset configuration described above with reference to FIG. 11D. The proximal edge portion 422-2 of the follower protrusion 422 contacts the distal edge 424-1 of the pusher protrusion 424, and the leader ramps 402-1, 402-2 are longitudinally spaced apart from, i.e. lead, the follower ramps 404-1, 404-2 by the offset amount. It will be appreciated that in operation, movement of the follower member 408 does not commence until the leader member 406 has moved the offset distance amount so as to bring the distal edge 424-1 into contact with the proximal edge 422-1 of the follower protrusion 422, whereupon the leader member 406 and the follower member 408 move in unison. Thus, the offset gap between the distal edge 424-1 and the proximal edge 422-1 achieves a lost motion effect in that the leader member 406 moves prior to movement of the follower member 408 even though both moved in response to drive rotation of the drive shaft 134.

It is noted that in FIG. 14B, the drive shuttle 144 already has progressed far enough distally that the leader ramps 402-1, 402-2 already have pushed up pushers 160 seated in some of the openings 106 in the downward facing surface 622-1 traversed by the leader side spacer beam 416. However, the follower ramps 404-1, 404-2, which are longitudinally offset to follow the leader ramps, have only partially pushed up pushers 160 seated in corresponding openings 106 in the downward facing surface 622-2 traversed by the follower side spacer beam 422.

Figure 15:
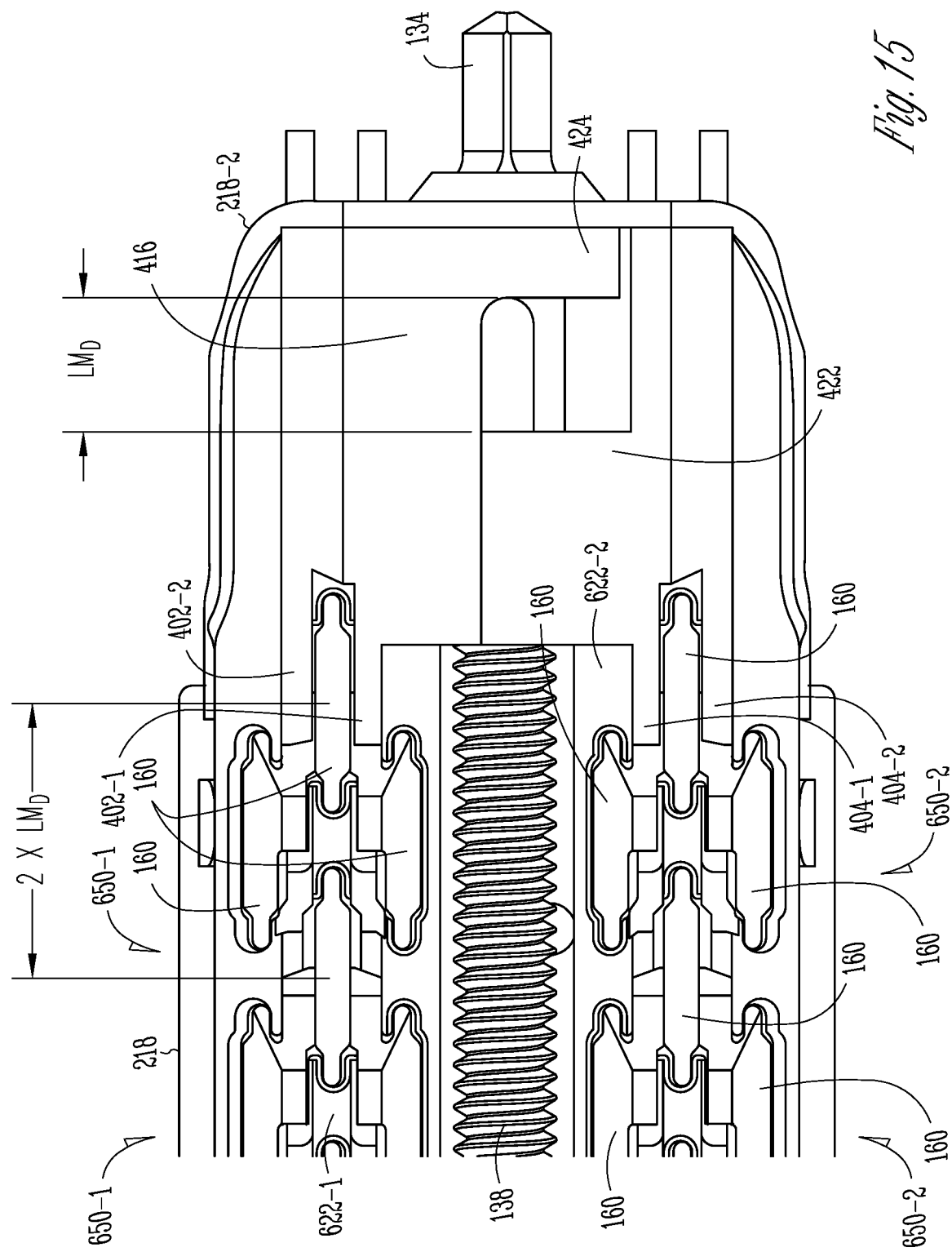
FIG. 15 is an illustrative bottom elevation view of the drive shuttle seated within the proximal end portion of the cartridge body in the aligned configuration described above with reference to FIG. 11C.

FIG. 15 is an illustrative bottom elevation view of the drive shuttle 144 seated within the proximal end portion 218-2 of the cartridge body 218 in the aligned configuration described above with reference to FIG. 11C. In accordance with some embodiments, the offset distance between the proximal edge portion 422-2 of the follower side spacer beam 422 and the distal edge 424-1 of the pusher protrusion 424 in the aligned configuration is selected to be one-half of the longitudinal spacing of the pushers 160. The pushers 160 and the staples 152 that they contain that are pushed by the leader ramps 402-1, 402-2 are situated in multiple longitudinal rows of openings 106 in the downward facing surface 622-1. The pushers 160 and the staples 152 that they contain that are pushed by the follower ramps 404-1, 404-2 are situated in multiple longitudinal rows of openings 106 in the downward facing surface 622-2.

In accordance with some embodiments, the cartridge body 218 defines three rows of pushers 160 set within corresponding rows of openings in each of the downward facing surfaces 622-1, 622-2 for a total of six rows of pushers 160. The longitudinal distance between openings 106 in each row and between pushers 160 disposed within the openings 106 in each row is the same for each row. In other words, each of the opening 106 and each of the corresponding pushers 160 in a given row is longitudinally spaced apart (i.e. in a direction parallel to the axis of the lead screw 134) by the same distance amount from its nearest neighbor openings 106 and pushers 160 in that row. Each staple 152 in each row in one of the downward facing surfaces 622-1 corresponds to a staple 152 in the other of the downward facing surfaces 622-2. Corresponding staples have identical rows—outer, middle, and inner and have the same longitudinal position within the row.

In accordance with some embodiments, an offset amount is selected so that the leader ramps 402-1, 402-2 and the follower ramps 404-1, 404-2 drive staples against the anvil face 220-1 at different times rather than simultaneously so as to reduce the instantaneous torque force within the end effector 210. Providing an offset distance between the leader ramps 402-1, 402-2 and the follower ramps 404-1, 404-2 ensures that they do not simultaneously reach, and therefore do not simultaneously deform, corresponding staples 152 in the different downward facing surface 622-1, 622-2. Referring to FIG. 15, a distance of $2 \times LM_D$ is indicated between two pushers 160 that are nearest longitudinal neighbors of each other in a middle row of the downward facing surface 622-1, which is twice the offset distance $LM_D$ indicated between the proximal edge portion 422-2 of the follower side spacer beam 422 and the distal edge 424-1 of the pusher protrusion 424. Using an offset that is one half the longitudinal spacing between neighbor staples in the same row ensures maximal separation in time between the moment when a staple in one of the downward facing surface 622-1, 622-2 is deformed by one of the leader ramps 402-1, 402-2 and the follower ramps 404-1, 404-2 and the moment at which a corresponding staple in the other of the downward facing surface 622-1, 622-2 is deformed by the other of the leader ramps 402-1, 402-2, thereby diminishing the chances of peak torque due to simultaneous deforming of such corresponding staples 152.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. An advanceable cam member comprising:
a leader ramp mount that includes a longitudinal first axis;
a first leader ramp physically coupled to a first lateral side of the leader ramp mount;
a pusher protrusion physically coupled to a second lateral side of the leader ramp mount;
a follower ramp mount;
a follower protrusion physically coupled to the follower ramp mount; and
a first follower ramp physically coupled to the follower protrusion;
wherein the first leader ramp, the pusher protrusion, the first follower ramp and the follower protrusion are disposed in relation to each other such that,
in a first configuration, the pusher protrusion is spaced apart longitudinally from the follower protrusion by an offset amount and the first leader ramp is aligned longitudinally with the first follower ramp, and
in a second configuration, the pusher protrusion contacts the follower protrusion and the first leader ramp is spaced apart longitudinally from the first, follower ramp by the offset amount.

2. The advanceable cam member of claim 1 further including:
a first guide component; and
a second guide component;
wherein the first and second guide components are configured to guide the leader ramp mount and the follower ramp mount between the first configuration and the second configuration.

3. The advanceable cam member of claim 2,
wherein the first guide component defines a slot; and
wherein the second guide component defines a rail.

4. The advanceable cam member of claim 2,
wherein the first guide component defines a slot;
wherein the second guide component defines a rail; and
wherein a longitudinal dimension of the first guide component and a longitudinal dimension of the second guide component differ by at least the offset amount.

5. The advanceable cam member of claim 2,
wherein the first guide component defines a rail; and
wherein the second guide component defines a slot.

6. The advanceable cam member of claim 2,
wherein the first guide component defines a rail;
wherein the second guide component defines a slot; and
wherein a longitudinal dimension of the first guide component and a longitudinal dimension of the second guide component differ by at least the offset amount.

7. The advanceable cam member of claim 2,
wherein the first guide component includes a proximal end and a distal end;
wherein in the first configuration, the second guide component contacts the distal end of the first guide component; and
wherein in the second configuration, the second guide component contacts the proximal end of the first guide component.

8. The advanceable cam member of claim 2,
wherein the first guide component includes a proximal end and a distal end; and
wherein the pusher protrusion is physically coupled to the second lateral side of the leader ramp mount that is adjacent the proximal end of the first guide component.

9. The advanceable cam member of claim 2, wherein the pusher protrusion includes a distal surface;
wherein the follower protrusion includes a proximal edge;
wherein the first guide component includes a proximal end and a distal end; and
wherein in the first configuration, the pusher protrusion distal surface is spaced apart longitudinally from the follower protrusion proximal edge by the offset amount and the second guide component contacts the distal end of the first guide component; and
wherein in the second configuration the pusher protrusion distal surface contacts the follower protrusion proximal edge and the second guide component contacts the proximal end of the first guide component.

10. The advanceable cam member of claim 2 further including:
a second leader ramp mounted adjacent to the first leader ramp; and
a second follower ramp mounted adjacent to the first follower ramp;
wherein the first and second leader ramps, the pusher protrusion, the first and second follower ramps and the follower protrusion are disposed in relation to each other while the second guide surface moveably contacts the first guide surface such that,
in the first configuration, the pusher protrusion is spaced apart longitudinally from the follower protrusion by an offset amount and the first and second leader ramps are aligned longitudinally with the first and second follower ramps, and
in the second configuration, the pusher protrusion contacts the follower protrusion and the first and second leader ramps are spaced apart longitudinally from the first and second follower ramps by the offset amount.

11. The advanceable cam member of claim 1,
wherein the pusher protrusion includes a distal surface; and
wherein the follower protrusion includes a proximal edge;
wherein in the first configuration, the pusher protrusion distal surface is spaced apart longitudinally from the follower protrusion proximal edge by the offset amount and the first leader ramp is aligned longitudinally with the first follower ramp; and
wherein in the second configuration, the pusher protrusion distal surface contacts the follower protrusion proximal edge and the first leader ramp is spaced apart longitudinally from the first follower ramp by the offset amount.

12. The advanceable cam member of claim 1 further including:
a second leader ramp mounted adjacent to the first leader ramp; and
a second follower ramp mounted adjacent to the first follower ramp.

13. The advanceable cam member of claim 1,
wherein the leader ramp mount having the first lateral side, and the second lateral side, further includes a front side, a back side, and an engagement surface configured to engage a drive mechanism to drive the leader ramp mount longitudinally parallel to the longitudinal first axis in a direction that passes through the front and back sides; further including:

wherein the leader ramp mount further includes a first guide component that includes a first guide surface; and wherein the follower ramp mount further includes a second guide component that includes a second guide surface that moveably contacts the first guide surface, wherein the first and second guide components are configured to cooperate to guide the leader ramp mount and the follower ramp mount between the first configuration and the second configuration while the drive mechanism drives the leader ramp mount longitudinally parallel to the first axis.

14. The advanceable cam member of claim 13, wherein the engagement surface includes a threaded portion configured to receive a lead screw drive mechanism.

15. The advanceable cam member of claim 13,
wherein the pusher protrusion includes a distal surface;
wherein the follower protrusion includes a proximal edge;
wherein in the first configuration, the pusher protrusion distal surface is spaced apart longitudinally from the follower protrusion proximal edge by the offset amount and the first leader ramp is aligned longitudinally with the first follower ramp; and
wherein in the second configuration, the pusher protrusion distal surface contacts the follower protrusion proximal edge and the first leader ramp is spaced apart longitudinally from the first follower ramp by the offset amount.

16. The advanceable cam member of claim 13,
wherein the first guide component defines a slot; and
wherein the second guide component defines a rail.

17. The advanceable cam member of claim 13,
wherein the first guide component defines a slot;
wherein the second guide component defines a rail; and
wherein a longitudinal dimension of the first guide component and a longitudinal dimension of the second guide component differ by at least the offset amount.

18. The advanceable cam member of claim 13,
wherein the first guide component defines a rail; and
wherein the second guide component defines a slot.

19. The advanceable cam member of claim 13,
wherein the first guide component defines a rail;
wherein the second guide component defines a slot; and
wherein a longitudinal dimension of the first guide component and a longitudinal dimension of the second guide component differ by at least the offset amount.

20. The advanceable cam member of claim 13,
wherein the first guide component includes a proximal end and a distal end;
wherein in the first configuration, the second guide component contacts the distal end of the first guide component; and
wherein in the second configuration, the second guide component contacts the proximal end of the first guide component.

21. The advanceable cam member of claim 13,
wherein the first guide component includes a proximal end and a distal end; and
wherein the pusher protrusion physically coupled to the second lateral side of the leader ramp mount that is adjacent the proximal end of the first guide component.

22. The advanceable cam member of claim 13,
wherein the pusher protrusion includes a distal surface;
wherein the follower protrusion includes a proximal edge;
wherein the first guide component includes a proximal end and a distal end; and
wherein in the first configuration, the pusher protrusion distal surface is spaced apart longitudinally from the follower protrusion proximal edge by the offset amount and the second guide component contacts the distal end of the first guide component; and
wherein in the second configuration the pusher protrusion distal surface contacts the follower protrusion proximal edge and the second guide component contacts the proximal end of the first guide component.

23. The advanceable cam member of claim 13 further including:
a second leader ramp mounted adjacent to the first leader ramp; and
a second follower ramp mounted adjacent to the first follower ramp.

24. The advanceable cam member of claim 13 further including:
a second leader ramp mounted adjacent to the first leader ramp; and
a second follower ramp mounted adjacent to the first follower ramp;
wherein the first and second leader ramps, the pusher protrusion, the first and second follower ramps and the follower protrusion are disposed in relation to each other while the second guide surface moveably contacts the first guide surface such that,
in the first configuration, the pusher protrusion is spaced apart longitudinally from the follower protrusion by an offset amount and the first and second leader ramps are aligned longitudinally with the first and second follower ramps; and
in the second configuration, the pusher protrusion contacts the follower protrusion and the first and second leader ramps are spaced apart longitudinally from the first and second follower ramps by the offset amount.

* * * * *